(12) United States Patent
Hansen et al.

(10) Patent No.: US 6,780,629 B2
(45) Date of Patent: *Aug. 24, 2004

(54) SUBTILASE ENZYMES

(75) Inventors: Peter Kamp Hansen, Lejre (DK); Peter Bauditz, Kobenhaven O (DK); Frank Mikkelsen, Valby (DK); Kim Vilbour Andersen, Copenhagen O (DK); Carsten Andersen, Vaerlose (DK); Mads Norregaard-Madsen, Odense M (DK)

(73) Assignee: Novozymes A/S, Bagsvaerd (DK)

( * ) Notice: Subject to any disclaimer, the term of this patent is extended or adjusted under 35 U.S.C. 154(b) by 2 days.

This patent is subject to a terminal disclaimer.

(21) Appl. No.: 10/243,576

(22) Filed: Sep. 13, 2002

(65) Prior Publication Data

US 2003/0191038 A1 Oct. 9, 2003

Related U.S. Application Data

(63) Continuation-in-part of application No. 09/574,468, filed on May 18, 2000, now abandoned, and a continuation-in-part of application No. 09/574,463, filed on May 18, 2000, now abandoned, and a continuation-in-part of application No. 09/574,143, filed on May 18, 2000, now abandoned, and a continuation-in-part of application No. 09/574,033, filed on May 18, 2000, now abandoned, and a continuation-in-part of application No. 09/573,932, filed on May 18, 2000, now abandoned, and a continuation-in-part of application No. 09/573,652, filed on May 18, 2000, now abandoned, and a continuation-in-part of application No. 09/573,299, filed on May 18, 2000, now abandoned, and a continuation-in-part of application No. 09/573,298, filed on May 18, 2000, now abandoned, and a continuation-in-part of application No. 09/196,281, filed on Nov. 19, 1998, now Pat. No. 6,605,458, said application No. 09/574,468, is a continuation-in-part of application No. 09/351,528, filed on Jul. 12, 1999, now abandoned, said application No. 09/574,463, is a continuation-in-part of application No. 09/351,825, filed on Jul. 12, 1999, now abandoned, said application No. 09/574,143, is a continuation-in-part of application No. 09/351,228, filed on Jul. 12, 1999, now abandoned, said application No. 09/574,033, is a continuation-in-part of application No. 09/351,527, filed on Jul. 12, 1999, now abandoned, said application No. 09/573,932, is a continuation-in-part of application No. 09/351,055, filed on Jul. 12, 1999, now abandoned, said application No. 09/573,652, is a continuation-in-part of application No. 09/351,054, filed on Jul. 12, 1999, now abandoned, said application No. 09/573,299, is a continuation-in-part of application No. 09/351,811, filed on Jul. 12, 1999, now abandoned, said application No. 09/573,298, is a continuation-in-part of application No. 09/351,595, filed on Jul. 12, 1999, now abandoned.

(30) Foreign Application Priority Data

| | | |
|---|---|---|
| Nov. 21, 1997 | (DK) | 1332/97 |
| May 20, 1999 | (DK) | 1999 00709 |
| May 20, 1999 | (DK) | 1999 00708 |
| May 20, 1999 | (DK) | 1999 00707 |
| May 20, 1999 | (DK) | 1999 00712 |
| May 20, 1999 | (DK) | 1999 00711 |
| May 20, 1999 | (DK) | 1999 00710 |
| May 20, 1999 | (DK) | 1999 00705 |
| May 20, 1999 | (DK) | 1999 00704 |

(51) Int. Cl.$^7$ .................. C12N 9/54; C12N 15/57; C12N 15/75; C11D 3/386

(52) U.S. Cl. ............ 435/220; 435/69.1; 435/221; 435/222; 435/253.2; 435/320.1; 435/471; 536/23.2; 510/350

(58) Field of Search ............... 435/220, 221, 435/222, 69.1, 252.3, 320.1; 434/471; 510/306, 350; 536/23.2

(56) References Cited

U.S. PATENT DOCUMENTS

| | | | |
|---|---|---|---|
| RE34,606 E | 5/1994 | Estell et al. | 435/222 |
| 5,543,302 A | 8/1996 | Boguslawski | 435/69.1 |
| 6,190,900 B1 * | 2/2001 | Sierkstra et al. | 435/221 |
| 6,558,938 B1 * | 5/2003 | Hansen et al. | 435/221 |
| 6,605,458 B1 * | 8/2003 | Hansen et al. | 435/220 |

FOREIGN PATENT DOCUMENTS

| | | |
|---|---|---|
| EP | 0 130 756 A1 | 1/1985 |
| EP | 01 214 435 A2 | 3/1987 |
| EP | 0 251 446 A2 | 1/1988 |
| EP | 0 260 105 B1 | 3/1988 |

| | | |
|---|---|---|
| EP | 0 405 901 | 1/1991 |
| EP | 0 525 610 A2 | 2/1993 |
| WO | WO 87/04461 | 7/1987 |
| WO | WO 87/05050 | 8/1987 |
| WO | WO 88/08028 | 10/1988 |
| WO | WO 88/08033 | 10/1988 |
| WO | WO 89/06279 | 7/1989 |
| WO | WO 91/00345 | 1/1991 |
| WO | WO 94/02618 | 2/1994 |
| WO | WO 95/27049 | 10/1995 |
| WO | WO 95/29979 | 11/1995 |
| WO | WO 95/30010 | 11/1995 |
| WO | WO 95/30011 | 11/1995 |
| WO | WO 96/28566 | 9/1996 |
| WO | WO 96/34935 | 11/1996 |

OTHER PUBLICATIONS

Meloun, B., et al., 1985, "Complete primary structure of thermitase from Thermoactinomyces vulgaris and its structural features related to the subtilisin–type proteinases", FEBS Letters, vol. 183, pp. 195–200.*

Koide, Y., et al., 1986, "Cloning and sequencing of the major intracellular serine protease gene of Bacillus subtilis", Journal of Bacteriology, vol. 167, pp. 110–116.*

Tatsumi, H., et al., 1989, "A full length cDNA clone for the alkaline protease of Aspergillus oryzae: Structural analysis and expression in Saccharomyces cerevisiae", Molecular and General Genetics, vol. 1219, pp. 33–38.*

Takekawa, S., et al., 1990, "Proteases involved in generation of [beta]– and [alpha]–amylases from a large amylase precursor in Bacillus polymyxa", Journal of Bacteriology, vol. 173, pp. 6820–6825.*

Siezen, R.J., et al., 1991, "Homology modeling and protein engineering strategy of subtilases, the family of subtilisin–like serine proteinases", Protein Engineering, vol. 4, pp. 719–737.*

Kato et al., 1992, PIR database Accession No. S27501.*

Schnell, N., et al., 1992, "Analysis of genes involved in the biosynthesis of lantobiotic epidermin", European Journal of Biochemistry, vol. 204, pp. 57–68.*

Whitby, P.W. et al., 1992, "The cloning and nucleotide sequence of the serine protease gene (aspA) of Aeromonas salmonicida ssp. salmonicida", FEMS Microbiology Letters, vol. 78, pp. 65–71.*

Geremia, R. A., et al., 1993, "Molecular characterization of the proteinase–encoding gene, prb1, related to mycoparasitism by Trichoderma haraianum", Molecular Microbiology, vol. 8, pp. 603–613.*

MacIver, B., et al., 1994, "Cloning and sequencing of a serine protease gene from a thermophilic Bacilus species and its expression in E. coli", Applied and Environmental Microbiology, vol. 60, pp. 3981–3988.*

Abraham, L.D., et al., 1995, "Factors affecting autolysis of a subtilisin–like serine proteinase secreted by Ophiosotoma picae and identification of the cleavage site", Biochimica et Biophysica Acta, vol. 1245, pp. 76–84.*

Piret et al., 1995, SPTREMBL database Accession No. Q53863.*

Kwon, Y.T., et al., 1995, "Cloning and characterization of the gene encoding an extracellular alkaline serine protease from Vibrio metschnikovii strain RH530", Gene, vol. 152, pp. 59–63.*

Gilbert, C., et al., 1996, "A new cell surface proteinase: Sequencing and analysis of the prtB gene from Lactobacillus delbrueckii subsp. bulgaricus", Journal of Bacteriology, vol. 178, pp. 3059–3065.*

Redenbach, M., et al., 1996, "A set of ordered cosmids and a detailed genetic and physical map for the 8 Mb Streptomyces coelicolor A3(2) chromosome", Molecular Microbiology, vol. 21, pp. 77–96/.*

Siezen, R.J., et al., 1997, "Subtilases: The superfamily of subtilisin–like serine proteases", Protein Science, vol. 6, pp. 501–523.*

Sloma et al., May 1997, SPTREMBL database Accession No. P97097.*

Russel et al. (1987) J. Mol. Biol. 193:803–813.

Russel et al. (1987) Nature 328(6):496–500.

Thomas et al. (1985) Nature 318(28):375–376.

Graycar et al., (1992) Annals New York Acad. of Sciences 672:71–79.

* cited by examiner

*Primary Examiner*—Nashaat T. Nashed
*Assistant Examiner*—William W. Moore
(74) *Attorney, Agent, or Firm*—Elias J. Lambris

(57) ABSTRACT

The present invention relates to subtilase enzymes of the I-S1 and I-S2 sub-groups having an additional amino acid in the active site loop (c) region from positions 125 to 132. The variant subtilases of the present invention exhibit improved wash performance in a detergent in comparison to its parent enzyme.

200 Claims, 5 Drawing Sheets

Figure 1A

```
No:     1         10        20        30        40        50
a)  AQSVPYGVSQIKAPALHSQGYTGSNVKVAVIDSGIDSSHPDLKVAGGASM
b)  AQSVPWGISRVQAPAAHNRGLTGSGVKVAVLDTGI*STHPDLNIRGGASF

No:           60        70        80        90        100
a)  VPSETNPFQDNNSHGTHVAGTVAALNNSIGVLGVAPSASLYAVKVLGADG
b)  VPGEPST*QDGNGHGTHVAGTIAALNNSIGVLGVAPSAELYAVKVLGASG

No:          110       120       130       140        150
a)  SGQYSWIINGIEWAIANNMDVINMSLGGPSGSAALKAAVDKAVASGVVVV
b)  SGSVSSIAQGLEWAGNNGMHVANLSLGSPSPSATLEQAVNSATSRGVLVV

No:          160       170       180       190        200
a)  AAAGNEGTSGSSSTVGYPGKYPSVIAVGAVDSSNQRASFSSVGPELDVMA
b)  AASGNSG*AGS***ISYPARYANAMAVGATDQNNNRASFSQYGAGLDIVA

No:          210       220       230       240        250
a)  PGVSIQSTLPGNKYGAYNGTSMASPHVAGAAALILSKHPNWTNTQVRSSL
b)  PGVNVQSTYPGSTYASLNGTSMATPHVAGAAALVKQKNPSWSNVQIRNHL

No:          260       270  275
a)  ENTTTKLGDSFYYGKGLINVQAAAQ
b)  KNTATSLGSTNLYGSGLVNAEAATR
```

```
No.:            10         20         30         40         50
a)    AQSVPYGVSQIKAPALHSQGYTGSNVKVAVIDSGIDSSHPDLKVAGGASM
g)    AQTVPYGIPLIKADKVQAQGFKGANVKVAVLDTGIQASHPDLNVVGGASF

No.:            60         70         80         90        100
a)    VPSETNPFQDNNSHGTHVAGTVAALNNSIGVLGVAPSASLYAVKVLGADG
g)    VAGEAYN*TDGNGHGTHVAGTVAALDNTTGVLGVAPSVSLYAVKVLNSSG

No.:           110        120        130        140        150
a)    SGQYSWIINGIEWAIANNMDVINMSLGGPSGSAALKAAVDKAVASGVVVV
b)    SGTYSGIVSGIEWATTNGMDVINMSLGGPSGSTAMKQAVDNAYARGVVVV

No.:           160        170        180        190        200
a)    AAAGNEGTSGSSSTVGYPGKYPSVIAVGAVDSSNQRASFSSVGPELDVMA
b)    AAAGNSGSSGNTNTIGYPAKYDSVIAVGAVDSNSNRASFSSVGAELEVMA

No.:           210        220        230        240        250
a)    PGVSIQSTLPGNKYGAYNGTSMASPHVAGAAALILSKHPNWTNTQVRSSL
b)    PGAGVYSTYPTSTYATLNGTSMASPHVAGAAALILSKHPNLSASQVRNRL

No.:           260        270  275
a)    ENTTTKLGDSFYYGKGLINVQAAAQ
b)    SSTATYLGSSFYYGKGLINVEAAAQ
```

SUBTILASE ENZYMES

CROSS-REFERENCE TO RELATED APPLICATIONS

This application is a continuation-in-part of Ser. Nos. 09/196,281 now U.S. Pat. No. 6,605,458, 09/574,463 abandoned, 09/573,932 abandoned, 09/574,143 abandoned, 09/574,468 abandoned, 09/574,033 abandoned, 09/573,652 abandoned, 09/573,298 abandoned, and 09/573,299 abandoned filed Nov. 19, 1998, May 18, 2000, May 18, 2000, May 18, 2000, May 18, 2000, May 18, 2000, May 18, 2000, May 18, 2000, and May 18, 2000, respectively, and claims, under 35 U.S.C. 119, priority of Danish application nos. 1332/97, PA 1999 00709, PA 1999 00708, PA 1999 00707, PA 1999 00712, PA 1999 00711, PA 1999 00710, PA 1999 00705 and PA 1999 00704 filed Nov. 21, 1997, May 20, 1999, May 20, 1999, May 20, 1999, May 20, 1999, May 20, 1999, May 20, 1999, May 20, 1999, and May 20, 1999, respectively. Application Ser. No. 09/574,463 is a continuation-in-part of application Ser. No. 09/351,825 filed Jul. 12, 1999 now abandoned. Application Ser. No. 09/573,932 is a continuation-in-part of application Ser. No. 09/351,055 filed Jul. 12, 1999 now abandoned. Application Ser. No. 09/574,143 is a continuation-in-part of application Ser. No. 09/351,228 filed Jul. 12, 1999 now abandoned. Application Ser. No. 09/574,468 is a continuation-in-part of application Ser. No. 09/351,528 filed Jul. 12, 1999 now abandoned. Application Ser. No. 09/574,033 is a continuation-in-part of application Ser. No. 09/351,527 filed Jul. 12, 1999 now abandoned. Application Ser. No. 09/573,652 is a continuation-in-part of application Ser. No. 09/351,054 filed Jul. 12, 1999 now abandoned. Application Ser. No. 09/573,298 is a continuation-in-part of application Ser. No. 09/351,595 filed Jul. 12, 1999 now abandoned. Application Ser. No. 09/573,299 is a continuation-in-part of application Ser. No. 09/351,811 filed Jul. 12, 1999 now abandoned. The contents of all of the above applications is incorporated herein by reference.

BACKGROUND OF THE INVENTION

1. Field of the Invention

The present invention relates to subtilase enzymes having an additional amino acid in the active site loop (c) region from position 125 to 132 and detergent and cleaning compositions comprising same. The invention further relates to genes coding for the expression of said enzymes when inserted into a suitable host cell or organism; and host cells transformed therewith, and methods for producing the enzymes.

2. Description of the Related Art

In the detergent industry, enzymes have been used in washing formulations for more than 30 years. Such enzymes include proteases, lipases, amylases, cellulases, as well as other enzymes, or mixtures thereof. The most important commercially are proteases.

An increasing number of commercially used proteases are protein engineered variants of naturally occurring wild-type proteases, e.g. DURAZYM® (Novo Nordisk A/S), RELASE® (Novo Nordisk A/S), MAXAPEM® (Gist-Brocades N.V.), PURAFECT® (Genencor International, Inc.).

In addition, a number of protease variants have been described in the art, such as in EP 130756 (GENENTECH) (corresponding to U.S. Reissue Pat. No. 34,606 (GENENCOR)); EP 214435 (HENKEL); WO 87/04461 (AMGEN); WO 87/05050 (GENEX); EP 260105 (GENENCOR); Thomas, Russell, and Fersht, *Nature,* 318, 375–376 (1985); Thomas, Russell, and Fersht, *J. Mol. Biol.,* 193, 803–813 (1987); Russel and Fersht, *Nature,* 328, 496–500 (1987); WO 88/08028 (Genex); WO 88/08033 (Amgen); WO 95/27049 (SOLVAY S.A.); WO 95/30011 (PROCTER & GAMBLE COMPANY); WO 95/30010 (PROCTER & GAMBLE COMPANY); WO 95/29979 (PROCTER & GAMBLE COMPANY); U.S. Pat. No. 5,543,302 (SOLVAY S.A.); EP 251 446 (GENENCOR); WO 89/06279 (NOVO NORDISK A/S); WO 91/00345 (NOVO NORDISK A/S); EP 525 610 A1 (SOLVAY) and WO 94/02618 (GIST-BROCADES N.V.).

However, even though a number of useful protease variants have been described, there is still a need for new improved proteases or protease variants for a number of industrial uses.

Therefore, an object of the present invention is to provide improved proteases or protein engineered protease variants, especially for use in the detergent industry.

SUMMARY OF THE INVENTION

The present inventors have found that subtilisins wherein at least one of the active site loops are longer than those presently known, exhibit improved wash performance properties in detergent compositions. The identification thereof was done by constructing subtilisin variants, especially of the subtilisin 309 (BLSAVI or SAVINASE®), which exhibited improved wash performance properties in detergent compositions relative to the parent wild-type enzyme. This has been described in our earlier application DK 1332/97, which published as WO 99/27082.

It has now been found that certain subtilases or variants thereof of the I-S1 (true "subtilisins") and I-S2 (high alkaline subtilisins) sub-groups having at least one additional amino acid residue in the active site loop (c) region from position 125 to 132, exhibit surprisingly improved wash performance in comparison to those presently known and those described in said application.

The improved proteases according to the invention may be obtained by isolation from natural resources or by the introduction of at least is one further amino acid residue (an insertion) in the active site loop (c) region in a wild-type subtilase (for a definition of the active site loops and the numbering of positions see below).

Although this finding was done in subtilisin 309, it is predicted that it will be possible to produce or isolate similar advantageous subtilases or subtilase variants.

Furthermore it will be possible to specifically screen natural isolates to identify wild-type subtilases comprising an active site loop (c) region which is longer than the corresponding active site loop in known wild-type subtilases, such as subtilisin 309, which subtilases can be considered to have an inserted amino acid residue in the active site loop (c) region, and exhibiting excellent wash performance in a detergent, in comparison to their closest related known subtilisin, such as subtilisin 309.

Concerning alignment and numbering, reference is made to FIGS. 1A, 1B, 2A and 2B showing alignments between subtilisin BPN' (BASBPN) (a) and subtilisin 309 (BLSAVI) (b), and alignments between subtilisin BPN' (a) (BASBPN) and subtilisin Carlsberg (g) (BLSCAR). These alignments are used herein as a reference for numbering the residues.

The seven active site loops (a) to (g) are herein defined as the segments of amino acid residues provided below (including the terminal amino acid residues):

(a) the region between amino acid residue 33 and 43;

(b) the region between amino acid residue 95 and 103;

(c) the region between amino acid residue 125 and 132;

(d) the region between amino acid residue 153 and 173;

(e) the region between amino acid residue 181 and 195;

(f) the region between amino acid residue 202 and 204;

(g) the region between amino acid residue 218 and 219.

Accordingly, in a first aspect the invention relates to an isolated (i.e. greater than 10% pure) subtilase enzyme of the I-S1 and I-S2 sub-groups having at least one additional amino acid residue in the active site loop (c) region from position 125 to 132, whereby said additional amino acid residue(s) corresponds to the insertion of at least one amino acid residue.

In a second aspect the invention relates to an isolated DNA sequence encoding a subtilase variant of the invention.

In a third aspect the invention relates to an expression vector comprising an isolated DNA sequence encoding a subtilase variant of the invention.

In a fourth aspect the invention relates to a microbial host cell transformed with an expression vector according to the third aspect.

In a further aspect the invention relates to the production of the subtilisin enzymes of the invention.

The enzymes of the invention can generally be produced by either cultivation of a microbial strain from which the enzyme was isolated and recovering the enzyme in substantially pure form; or by inserting an expression vector according to the third aspect of the invention into a suitable microbial host, cultivating the host to express the desired subtilase enzyme, and recovering the enzyme product.

Further the invention relates to a composition comprising a subtilase or subtilase variant of the invention.

Even further the invention relates to the use of the enzymes of the invention for a number of industrial relevant uses, in particular for use in cleaning and detergent compositions, comprising the subtilisin enzymes of the present invention.

Definitions

Prior to discussing this invention in further detail, the following terms and conventions will first be defined.

| NOMENCLATURE OF AMINO ACIDS | | |
|---|---|---|
| A = | Ala = | Alanine |
| V = | Val = | Valine |
| L = | Leu = | Leucine |
| I = | Ile = | Isoleucine |
| P = | Pro = | Proline |
| F = | Phe = | Phenylalanine |
| W = | Trp = | Tryptophan |
| M = | Met = | Methionine |
| G = | Gly = | Glycine |
| S = | Ser = | Serine |
| T = | Thr = | Threonine |
| C = | Cys = | Cysteine |
| Y = | Tyr = | Tyrosine |
| N = | Asn = | Asparagine |
| Q = | Gln = | Glutamine |
| D = | Asp = | Aspartic Acid |
| E = | Glu = | Glutamic Acid |
| K = | Lys = | Lysine |
| R = | Arg = | Arginine |
| H = | His = | Histidine |
| X = | Xaa = | Any amino acid |

| NOMENCLATURE OF NUCLEIC ACIDS | | |
|---|---|---|
| A = | Adenine | |
| G = | Guanine | |
| C = | Cytosine | |
| T = | Thymine | (only in DNA) |
| U = | Uracil | (only in RNA) |

Nomenclature and Conventions for Designation of Variants

In describing the subtilases of the present invention, the following nomenclatures and conventions have been adapted for ease of reference:

A frame of reference is first defined by aligning the isolated or parent wild-type enzyme with subtilisin BPN' (BASBPN).

The alignment can be obtained by the GAP routine of the GCG package version 9.1 to number the variants using the following parameters: gap creation penalty=8 and gap extension penalty=8 and all other parameters kept at their default values.

Another method is to use known recognized alignments between subtilases, such as the alignment indicated in WO 91/00345. In most is cases the differences will not be of any importance.

Such alignments between subtilisin BPN' (BASBPN) and subtilisin 309 (BLSAVI) and subtilisin Carlsberg (BLSCAR), respectively are indicated in FIGS. 1A, 1B, 2A, and 2B. They define a number of deletions and insertions in relation to BASBPN. In FIG. 1A, subtilisin 309 has 6 deletions in positions 36, 58, 158, 162, 163, and 164 in comparison to BASBPN, whereas in FIG. 1B subtilisin 309 has the same deletions in positions 36, 56, 159, 164, 165, and 166 in comparison to BASBPN. In FIG. 2A subtilisin Carlsberg has one deletion in position 58 in comparison to BASBPN, whereas in FIG. 2B subtilisin Carlsberg has the one deletion in position 56 in comparison to BASBPN. These deletions are indicated in FIGS. 1A, 1B, 2A, and 2B by asterisks (*).

The various modifications performed in a wild-type enzyme are indicated in general using three elements as follows:

Original Amino Acid Position Substituted Amino Acid

Thus, the notation G195E means a substitution of glycine in position 195 with glutamic acid.

In the case when the original amino acid residue may be any amino acid residue, a short hand notation may at times be used indicating only the position and substituted amino acid, Position Substituted Amino Acid Such a notation is particularly relevant in connection with modification(s) in homologous subtilases (vide infra).

Similarly when the identity of the substituting amino acid residue(s) is immaterial, the following short hand notation can be used:

Original Amino Acid Position

When both the original amino acid(s) and substituted amino acid(s) may comprise any amino acid, then only the position is indicated, e.g., 170.

When the original amino acid(s) and/or substituted amino acid(s) may comprise more than one, but not all amino acid(s), then the selected amino acids are indicated inside brackets { }, Original Amino Acid Position Substituted Amino Acid$_p$, . . . ,
Substituted Amino Acid$_n$ For specific variants the specific three or one letter codes are used, including the codes Xaa and X to indicate any amino acid residue.

Substitutions:

The substitution of glutamic acid for glycine in position 195 is designated as:

Gly195Glu or G195E or the substitution of any amino acid residue acid for glycine in position 195 is designated as:

Gly195Xaa or G195X or Gly195 or G195

The substitution of serine for any amino acid residue in position 170 would thus be designated Xaa170Ser or X170S or 170Ser or 170S.

Thus, 170Ser comprises e.g. both a Lys170Ser modification in BASBPN and an Arg170Ser modification in BLSAVI (cf. FIG. 1).

For a modification where the original amino acid(s) and/or substituted amino acid(s) may comprise more than one, but not all amino acid(s), the substitution of glycine, alanine, serine or threonine for arginine in position 170 would be indicated by Arg170{Gly,Ala,Ser,Thr} or R170{G,A,S,T} to indicate the variants

R170G, R170A, R170S, and R170T.

Deletions:

A deletion of glycine in position 195 is indicated by:

Gly195*or G195*

Similarly, the deletion of more than one amino acid residue, such as the deletion of glycine and leucine in positions 195 and 196 is designated Gly195*+Leu196* or G195*+L196*

Insertions:

The insertion of an additional amino acid residue such as e.g. a lysine after G195 is designated:

Gly195GlyLys or G195GK; or when more than one amino acid residue is inserted, such as e.g. a Lys, Ala and Ser after G195 this is shown as:

Gly195GlyLysAlaSer or G195GKAS (SEQ ID NO: 1)

In such cases the inserted amino acid residue(s) are numbered by the addition of lower case letters to the position number of the amino acid residue preceding the inserted amino acid residue(s). In the above example the sequences 194 to 196 would thus be:

|        | 194 | 195 | 195a | 195b | 195c | 196 |
|--------|-----|-----|------|------|------|-----|
| BLSAVI | A - | G - |      |      |      | L   |
| Variant| A - | G - | K -  | A -  | S -  | L   (SEQ ID NO: 2) |

In cases where an amino acid residue identical to the existing amino acid residue is inserted it is clear that a degeneracy in the nomenclature arises. If for example a glycine is inserted after the glycine in the above example this would be indicated by G195GG. The same actual change could just as well be indicated as A194AG for the change from

|        | 194 | 195 | 196 |
|--------|-----|-----|-----|
| BLSAVI | A - | G - | L   | to

|        | 194 | 195  | 195a | 196 |
|--------|-----|------|------|-----|
| Variant| A - | G -  | G -  | L   (SEQ ID NO: 3) |
|        | 194 | 194a | 195  | 196 |

Such instances will be apparent to the skilled person. Thus, it is to be understood that the indication G195GG and corresponding indications encompass such equivalent degenerate indications.

Sometimes it is desired to both perform a modification and an insertion at the same position. This situation is also covered by the present definitions. Thus, S130TP indicates that the serine in position 130 has been replaced by a tyrosine and a proline. Another way to describe this variant is S130SP+S130T.

Filling a Gap:

Where a deletion in an enzyme exists in the reference comparison with the subtilisin BPN' sequence used for the numbering, an insertion in such a position is indicated as:

*36Asp or *36D for the insertion of an aspartic acid at position 36.

Multiple Modifications

Variants comprising multiple modifications are separated by pluses, e.g.:

Arg170Tyr+Gly195Glu or R170Y+G195E representing modifications in positions 170 and 195 substituting tyrosine and glutamic acid for arginine and glycine, respectively, or e.g. Tyr167{Gly,Ala,Ser,Thr}+Arg170{Gly,Ala,Ser,Thr} designates the variants Tyr167Gly+Arg170Gly, Tyr167Gly+Arg170Ala, Tyr167Gly+Arg170Ser, Tyr167Gly+Arg170Thr, Tyr167Ala+Arg170Gly, Tyr167Ala+Arg170Ala, Tyr167Ala+Arg170Ser, Tyr167Ala+Arg170Thr, Tyr167Ser+Arg170Gly, Tyr167Ser+Arg170Ala, Tyr167Ser+Arg170Ser, Tyr167Ser+Arg170Thr, Tyr167Thr+Arg170Gly, Tyr167Thr+Arg170Ala, Tyr167Thr+Arg170Ser, and Tyr167Thr+Arg170Thr.

This nomenclature is particularly relevant for designating modifications that are substitutions, insertions or deletions of amino acid residues having specific common properties, such as residues of positive charge (K, R, H), negative charge (D, E), or conservative amino acid modification(s) of e.g. Tyr167{Gly,Ala,Ser,Thr}+Arg170{Gly,Ala,Ser,Thr}, which signifies substituting a small amino acid for another small amino acid. See section "Detailed description of the invention" for further details.

Numbering of Amino Acid Positions/Residues

For purposes of this invention, the numbering of amino acids corresponds to that of the amino acid sequence of subtilase BPN' (BASBPN). For further description of the amino acid sequence of subtilisin BPN', see FIGS. 1 and 2, or Siezen et al., *Protein Engng.*, 4, 719–737 (1991).

Proteases

Enzymes cleaving the amide linkages in protein substrates are classified as proteases, or (interchangeably) peptidases (see Walsh, 1979, *Enzymatic Reaction Mechanisms*. W. H. Freeman and Company, San Francisco, Chapter 3).

Serine Proteases

A serine protease is an enzyme which catalyzes the hydrolysis of peptide bonds, and in which there is an essential serine residue at the active site (White, Handler and Smith, *"Principles of Biochemistry,"* Fifth Edition, McGraw-Hill Book Company, NY, pp. 271–272 (1973)).

The bacterial serine proteases have molecular weights in the 20,000 to 45,000 Dalton range. They are inhibited by diisopropylfluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest, *Bacteriological Rev.,* 41, 711–753 (1977)).

Subtilases

A sub-group of the serine proteases tentatively designated subtilases has been proposed by Siezen et al., *Protein Engng.,* 4, 719–737 (1991) and Siezen et al., *Protein Science,* 6, 501–523 (1997). They are defined by homology analysis of more than 170 amino acid sequences of serine proteases previously referred to as subtilisin-like proteases. A subtilisin was previously often defined as a serine protease produced by gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997).

One subgroup of the subtilases, I-S1 or "true#" subtilisins, comprises the "classical" subtilisins, such as subtilisin 168 (BSS168), subtilisin BPN', subtilisin Carlsberg (ALCALASE®, NOVO NORDISK A/S), and subtilisin DY (BSSDY).

A further subgroup of the subtilases, I-S2 or high alkaline subtilisins, is recognized by Siezen et al. Sub-group I-S2 proteases are described as highly alkaline subtilisins and comprises enzymes such as subtilisin PB92 (BAALKP) (MAXACAL®, Gist-Brocades NV), subtilisin 309 (SAVINASE®, NOVO NORDISK A/S), subtilisin 147 (BLS147) (ESPERASE®, NOVO NORDISK A/S), and alkaline elastase YaB (BSEYAB).

List of Acronyms for Subtilases:

I-S1

Subtilisin 168, BSS168 (BSSAS (Subtilisin amylosacchariticus)), BSAPRJ (Subtilisin J), BSAPRN (Subtilisin NAT), BMSAMP (Mesentericopeptidase),
Subtilisin BPN', BASBPN,
Subtilisin DY, BSSDY,
Subtilisin Carlsberg, BLSCAR (BLKERA (Keratinase), BLSCA1, BLSCA2, BLSCA3),
BSSPRC, Serine protease C
BSSPRD, Serine protease D

I-S2

Subtilisin Sendai, BSAPRS
Subtilisin ALP 1, BSAPRQ,
Subtilisin 147, Esperase®, BLS147 (BSAPRM (SubtilisinAprM), BAH101)
Subtilisin 309, SAVINASE®, BLS309/BLSAVI (BSKSMK (M-protease), BAALKP (Subtilisin PB92, Bacillus alkalophilic alkaline protease), BLSUBL (Subtilisin BL)),
Alkaline elastase YaB, BYSYAB

"SAVINASE®"

SAVINASE® is marketed by NOVO NORDISK A/S. It is subtilisin 309 from *B. lentus* and differs from BAALKP only in one position (N87S, see FIG. 1). SAVINASE® has the amino acid sequence designated b) in FIG. 1.

Parent Subtilase

The term "parent subtilase" describes a subtilase defined according to Siezen et al. (1991 and 1997). For further details see description of "SUBTILASES" immediately above. A parent subtilase may also be a subtilase isolated from a natural source, wherein subsequent modification have been made while retaining the characteristic of a subtilase. Alternatively the term "parent subtilase" may be termed "wild-type subtilase".

Modification(s) of a Subtilase Variant

The term "modification(s)" used herein is defined to include chemical modification of a subtilase as well as genetic manipulation of the DNA encoding a subtilase. The modification(s) can be replacement(s) of the amino acid side chain(s), substitution(s), deletion(s) and/or insertions in or at the amino acid(s) of interest.

Subtilase Variant

In the context of this invention, the term subtilase variant or mutated subtilase means a subtilase that has been produced by an organism which is expressing a mutant gene derived from a parent microorganism which possessed an original or parent gene and which produced a corresponding parent enzyme, the parent gene having been mutated in order to produce the mutant gene from which said mutated subtilase protease is produced when expressed in a suitable host.

Homologous Subtilase Sequences

The present invention relates to modified subtilases comprising an insertion in the active site loop (b) region in the subtilase SAVINASE® and other parent (wild-type) subtilases, which have a homologous primary structure to that of SAVINASE®. The homology between two amino acid sequences is in this context described by the parameter "identity".

In order to determine the degree of identity between two subtilases the GAP routine of the GCG package version 9.1 can be applied using the same settings as indicated above. The output from the routine is besides the amino acid alignment the calculation of the "Percent Identity" between the two sequences.

Based on this description it is routine for a person skilled in the art to identify suitable homologous subtilases and corresponding homologous active site loop regions, which can be modified according to the invention.

Wash Performance

The ability of an enzyme to catalyze the degradation of various naturally occurring substrates present on the objects to be cleaned during e.g. wash or hard surface cleaning is often referred to as its washing ability, wash-ability, detergency, or wash performance. Throughout this application the term wash performance will be used to encompass this property.

Isolated DNA Sequence

The term "isolated", when applied to a DNA sequence molecule, denotes that the DNA sequence has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, Nature, 316, 774–78 (1985)). The term "an isolated DNA sequence" may alternatively be termed "a cloned is DNA sequence".

Isolated Protein

When applied to a protein, the term "isolated" indicates that the protein has been removed from its native environment.

In a preferred form, the isolated protein is substantially free of other proteins, particularly other homologous proteins (i.e. "homologous impurities" (see below)).

An isolated protein is greater than 10% pure, preferably greater than 20% pure, more preferably greater than 30% pure, as determined by SDS-PAGE. Further it is preferred to provide the protein in a highly purified form, i.e., greater than 40% pure, greater than 60% pure, greater than 80% pure, more preferably greater than 95% pure, and even more preferably greater than 99% pure, as determined by SDS-PAGE.

The term "isolated protein" may alternatively be termed "purified protein".

Homologous Impurities

The term "homologous impurities" means any impurity (e.g. a polypeptide other than the polypeptide of the invention) which originates from the homologous cell where the polypeptide of the invention is originally obtained from.

Obtained From

The term "obtained from" as used herein in connection with a specific microbial source, means that the polynucleotide and/or polypeptide is produced by the specific source, or by a cell in which a gene from the source has been inserted.

Substrate

The term "Substrate" used in connection with a substrate for a protease should be interpreted in its broadest form as comprising a compound containing at least one peptide bond susceptible to hydrolysis by a subtilisin protease.

Product

The term "product" used in connection with a product derived from a protease enzymatic reaction should in the context of this invention be interpreted to include the products of a hydrolysis reaction involving a subtilase protease. A product may be the substrate in a subsequent hydrolysis reaction.

BRIEF DESCRIPTION OF THE DRAWINGS

FIG. 1A shows an alignment of subtilisin BPN' (a) (SEQ ID NO: 4) and SAVINASE® (b) (SEQ ID NO: 5) using the GAP routine mentioned above.

FIG. 1B shows the alignment of subtilisin BPN' (SEQ ID NO: 4) and SAVINASE® (SEQ ID NO: 5) as taken from WO 91/00345.

FIG. 2A shows an alignment of subtilisin BPN' (SEQ ID NO: 4) and subtilisin Carlsberg (SEQ ID NO: 6) using the GAP routine mentioned above.

FIG. 2B shows the alignment of subtilisin BPN' (SEQ ID NO: 4) and subtilisin Carlsberg (SEQ ID NO: 6) as taken from WO 91/00345.

DETAILED DESCRIPTION OF THE INVENTION

Figure 3:
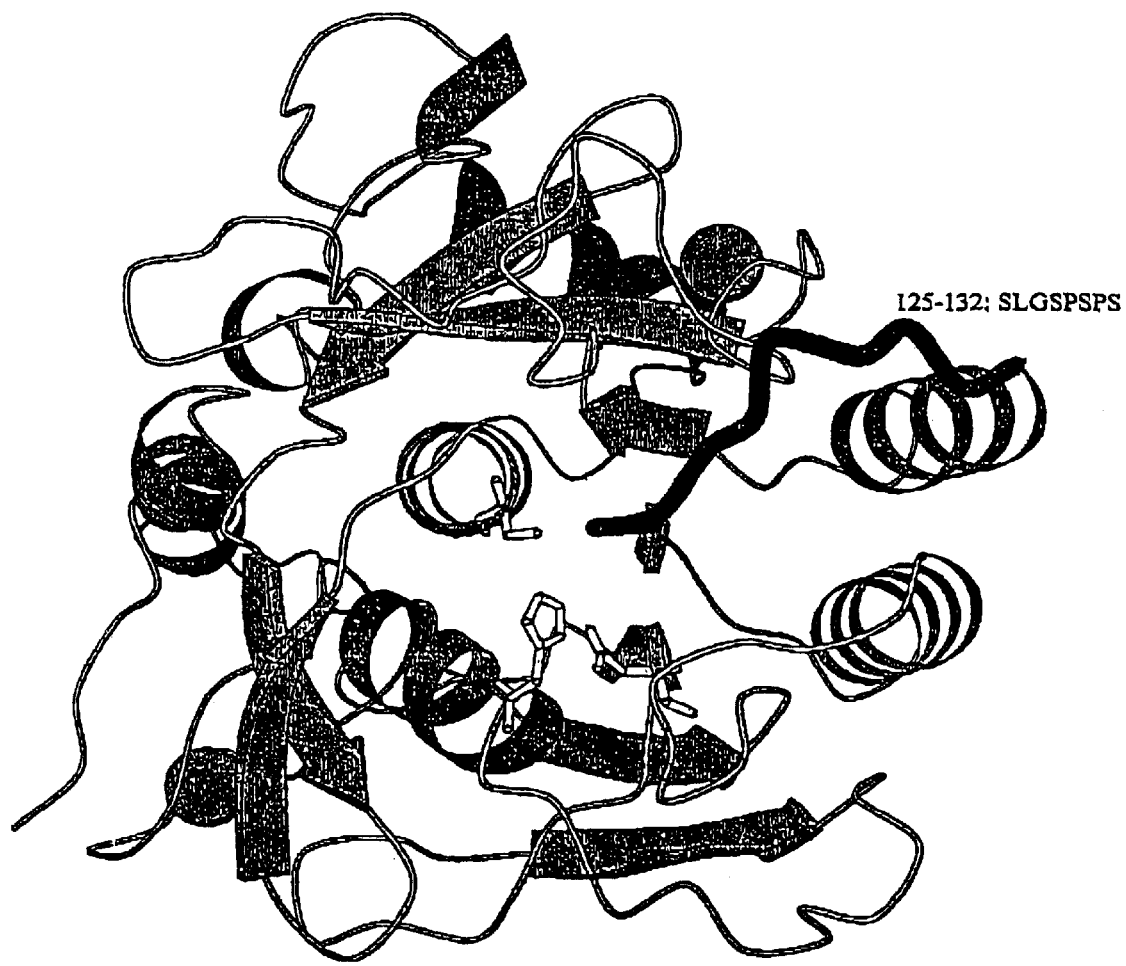
FIG. 3 shows the three dimensional structure of SAVINASE (Protein data bank (PDB) entry 1SVN), which indicates the active site loop (c) region.

The subtilases of the invention in a first aspect relates to an isolated (i.e. greater than 10% pure) subtilase enzyme of the I-S1 and I-S2 sub-groups having at least one additional amino acid residue in the active site loop (c) region from position 125 to 132, whereby said additional amino acid residue(s) correspond to the insertion of at least one amino acid residue.

In other words the subtilases of the invention are characterized by comprising an active site loop (c) region of more than 8 amino acid residues.

In a preferred embodiment, the subtilases of the present invention have at least one additional amino acid residue between positions 125 and 126.

In a preferred embodiment, the subtilases of the present invention have at least one additional amino acid residue between positions 126 and 127.

In a preferred embodiment, the subtilases of the present invention have at least one additional amino acid residue between positions 127 and 128.

In a preferred embodiment, the subtilases of the present invention have at least one additional amino acid residue between positions 128 and 129.

In a preferred embodiment, the subtilases of the present invention have at least one additional amino acid residue between positions 129 and 130.

In a preferred embodiment, the subtilases of the present invention have at least one additional amino acid residue between positions 130 and 131.

In a preferred embodiment, the subtilases of the present invention have at least one additional amino acid residue between positions 131 and 132.

In a preferred embodiment, the subtilases of the present invention have at least one additional amino acid residue between positions 132 and 133.

A subtilase of the first aspect of the invention may be a parent or wild-type subtilase identified and isolated from nature.

Such a parent wild-type subtilase may be specifically screened for by standard techniques known in the art.

One preferred way of doing this may be by specifically PCR amplify DNA regions known to encode active site loops in subtilases from numerous different microorganism, preferably different Bacillus strains.

Subtilases are a group of conserved enzymes, in the sense that their DNA and amino acid sequences are homologous. Accordingly it is possible to construct relatively specific primers flanking active site loops.

One way of doing this is by investigating an alignment of different subtilases (see e.g. Siezen et al., Protein Science, 6, 501–523 (1997)). It is from this routine work for a person skilled in the art to construct PCR primers flanking the active site loop corresponding to the active site loop (c) region between amino acid residues 125 and 132 in an I-S1 or I-S2 group subtilase, such as from BLSAVI. Using such PCR primers to amplify DNA from a number of different microorganism, preferably different Bacillus strains, followed by DNA sequencing of said amplified PCR fragments, it will be possible to identify strains which produce subtilases of these groups comprising a longer, as compared to e.g. BLSAVI, active site region corresponding to the active site loop (c) region from position 125 to 132. Having identified the strain and a partial DNA sequence of such a subtilase of interest, it is routine work for a person skilled in the art to complete cloning, expression and purification of such a subtilase of the invention.

However, it is envisaged that a subtilase enzyme of the invention predominantly is a variant of a parent subtilase.

Accordingly, in one embodiment the invention relates to an isolated subtilase enzyme according to the first aspect of the invention, wherein said subtilase enzyme is a constructed variant having a longer active site loop (c) region than its parent enzyme.

The subtilases of the invention exhibit excellent wash performance in a detergent, and if the enzyme is a constructed variant an improved wash performance in a detergent in comparison to its closest related subtilase, such as subtilisin 309.

Different subtilase products will exhibit a different wash performance in different types of detergent compositions. A subtilase of the invention has improved wash performance, as compared to its closest relative in a majority of such different types of detergent compositions.

Preferably, a subtilase enzyme of the invention has improved wash performance, as compared to its closest relative in the detergent compositions described in Example 3.

In order to determine if a given subtilase amino acid sequence (irrelevant whether said subtilase sequence is a parent wild-type subtilase sequence or a subtilase variant sequence produced by any other method than by site directed mutagenesis) is within the scope of the invention, the following procedure may be used:

(a) align said subtilase sequence to the amino acid sequence of subtilisin BPN';

(b) based on the alignment performed in step (a) identify the active site loop (c) region, in said subtilase sequence corresponding to the active site loop (c) region of subtilisin BPN' comprising the region between amino acid residues 125 and 132 (both of the end amino acids included);

(c) determine if the active site loop (c) region in said subtilase sequence, identified in step (b) is longer than the corresponding active site loop region in subtilisin BPN'.

If this is the case the subtilase investigated is a subtilase within the scope of the present invention.

The alignment performed in step (a) above is performed as described above by using the GAP routine.

Based on this description it is routine for a person skilled in the art to identify the active site loop (c) region in a subtilase and determine if the subtilase in question is within the scope of the invention. If a variant is constructed by site directed mutagenesis, it is of course known beforehand if the subtilase variant is within the scope of the invention.

A subtilase variant of the invention may be constructed by standard techniques known in the art such as by site-directed/random mutagenesis or by DNA shuffling of different subtilase sequences. See sections "PRODUCING A SUBTILASE VARIANT" and "Materials and Methods" for further details.

In further embodiments the invention relates to (a) an isolated subtilase enzyme according to the invention, wherein said at least one inserted amino acid residue is selected from the group comprising: A, G, S, and T;

(b) an isolated subtilase enzyme according to the invention, wherein said at least one inserted amino acid residue is selected from the group of charged amino acid residues comprising: D, E, H, K, and R, more preferably D, E, K and R;

(c) an isolated subtilase enzyme according to the invention, wherein said at least one inserted amino acid residue is selected from the group of hydrophilic amino acid residues comprising: C, N, Q, S, and T, more preferably N, Q, S and T;

(d) an isolated subtilase enzyme according to the invention, wherein said at least one inserted amino acid residue is selected from the group of small hydrophobic amino acid residues comprising: A, G and V; or (e) an isolated subtilase enzyme according to the invention, wherein said at least one inserted amino acid residue is selected from the group of large hydrophilic amino acid residues comprising: F, I, L, M, P, W and Y, more preferably F, I, L, M, and Y.

In a further embodiment, the invention relates to an isolated subtilase enzyme according to the invention, wherein said insertion comprises at least two amino acids, as compared to the corresponding active site loop region in subtilisin BPN'.

In further embodiments the invention relates to an isolated subtilase enzyme comprising at least one insertion, selected from the group comprising (in BASBPN numbering):

X125X{T,G,A,S}
X125X{D,E,K,R}
X125X{H,V,C,N,Q}
X125X{F,I,L,M,P,W,Y}
X126X{T,G,A,S}
X126X{D,E,K,R}
X126X{H,V,C,N,Q}
X126X{F,I,L,M,P,W,Y}
X127X{T,G,A,S}
X127X{D,E,K,R}
X127X{H,V,C,N,Q}
X127X{F,I,L,M,P,W,Y}
X128X{T,G,A,S}
X128X{D,E,K,R}
X128X{H,V,C,N,Q}
X128X{F,I,L,M,P,W,Y}
X129X{T,G,A,S}
X129X{D,E,K,R}
X129X{H,V,C,N,Q}
X129X{F,I,L,M,P,W,Y}
X130X{T,G,A,S}
X130x{D,E,K,R}
X130x{H,V,C,N,Q}
X130X{F,I,L,M,P,W,Y}
X131X{T,G,A,S}
X131x{D,E,K,R}
X131X{H,V,C,N,Q}
X131X{F,I,L,M,P,W,Y}
X132X{T,G,A,S}
X132X{D,E,K,R}
X132X{H,V,C,N,Q}
X132X{F,I,L,M,P,W,Y} or more specific for subtilisin 309 and closely related subtilases, such as BAALKP, BLSUBL, and BSKSMK

S125SA
S125ST
S125SG
S125SS
S125SD
S125SE
S125SK
S125SR
S125SH
S125SV

S125SC
S125SN
S125SQ
S125SF
S125SI
S125SL
S125SM
S125SP
S125SW
S125SY
L126LA
L126LT
L126LG
L126LS
L126LD
L126LE
L126LK
L126LR
L126LH
L126LV
L126LC
L126LN
L126LQ
L126LF
L126LI
L126LL
L126LM
L126LP
L126LW
L126LY
G127GA
G127GT
G127GG
G127GS
G127GD
G127GE
G127GK
G127GR
G127GH
G127GV
G127GC
G127GN
G127GQ
G127GF
G127GI
G127GL
G127GM
G127GP
G127GW
G127GY
S128SA
S128ST
S128SG
S128SS
S128SD
S128SE

S128SK
S128SR
S128SH
S128SV
S128SC
S128SN
S128SQ
S128SF
S128SI
S128SL
S128SM
S128SP
S128SW
S128SY
P129PA
P129PT
P129PG
P129PS
P129PD
P129PE
P129PK
P129PR
P129PH
P129PV
P129PC
P129PN
P129PQ
P129PF
P129PI
P129PL
P129PM
P129PP
P129PW
P129PY
S130SA
S130ST
S130SG
S130SS
S130SD
S130SE
S130SK
S130SR
S130SH
S130SV
S130SC
S130SN
S130SQ
S130SF
S130SI
S130SL
S130SM
S130SP
S130SW
S130SY
P131PA
P131PT

P131PG
P131PS
P131PD
P131PE
P131PK
P131PR
P131PH
P131PV
P131PC
P131PN
P131PQ
P131PF
P131PI
P131PL
P131PM
P131PP
P131PW
P131PY
S132SA
S132ST
S132SG
S132SS
S132SD
S132SE
S132SK
S132SR
S132SH
S132SV
S132SC
S132SN
S132SQ
S132SF
S132SI
S132SL
S132SM
S132SP
S132SW
S132SY

Furthermore the invention relates to subtilases comprising multiple insertions at any of positions 125, 126, 127, 128, 129, 130, 131 and 132, or any of the following combinations:

G70C+S128A+P129T+S130T+P131STR
S106W+G127GS+P129A
S125SA+P129S
S125SSP+P129G
L126LA+P129S
G127GS+P129A+S130T
S128A+P131PTA
S128SA+P129S+S130T+S132A
S128SD+P129PR
S128ST+P129S
S128ST+P129S+P131A
S128STT+P129S+S130A+P131T
S128T+S130A+P131T+S132STP
P129G+S130SSP
P129PAH
P129PAS
P129PHG
P129S+S130SA
P129S+S130TP
S130SHQ
S130SLA+P131A
S130SNN+P131H
S130ST+Y167A
S130STT

It is well known in the art that a so-called conservative substitution of one amino acid residue to a similar amino acid residue is expected to produce only a minor change in the characteristic of the enzyme.

Table III below list groups of conservative amino acid substitutions.

TABLE III

Conservative amino acid substitutions

| Common Property | Amino Acid |
|---|---|
| Basic (positive charge) | K = lysine |
| | H = histidine |
| Acidic (negative charge) | E = glutamic acid |
| | D = aspartic acid |
| Polar | Q = glutamine |
| | N = asparagines |
| Hydrophobic | L = leucine |
| | I = isoleucine |
| | V = valine |
| | M = methionine |
| Aromatic | F = phenylalanine |
| | W = tryptophan |
| | Y = tyrosine |
| Small | G = glycine |
| | A = alanine |
| | S = serine |
| | T = threonine |

According to this principle, subtilase variants comprising conservative substitutions, such as G97A+A98AS+S99G and G97S+A98AT+S99A are expected to exhibit characteristics that are not drastically different from each other.

Based on the disclosed and/or exemplified subtilase variants herein, it is routine work for a person skilled in the art to identify suitable conservative modification(s) to these variants in order to obtain other subtilase variants exhibiting similarly improved wash-performance.

According to the invention, the subtilases of the invention belong to the subgroups I-S1 and I-S2, especially subgroup I-S2, both for isolating novel enzymes of the invention from nature or from the artificial creation of diversity, and for designing and producing is variants from a parent subtilase.

In relation to variants from subgroup I-S1, it is preferred to choose a parent subtilase from the group comprising BSS168 (BSSAS, BSAPRJ, BSAPRN, BMSAMP), BASBPN, BSSDY, BLSCAR (BLKERA, BLSCA1, BLSCA2, BLSCA3), BSSPRC, and BSSPRD, or functional variants thereof having retained the characteristic of subgroup I-S1.

In relation to variants from subgroup I-S2 it is preferred to choose a parent subtilase from the group comprising BSAPRQ, BLS147 (BSAPRM, BAH101), BLSAVI (BSKSMK, BAALKP, BLSUBL), BYSYAB, and BSAPRS, or functional variants thereof having retained the characteristic of sub-group I-S2.

In particular, said parent subtilase is BLSAVI (SAVINASE®, NOVO NORDISK A/S), and a preferred subtilase variant of the invention is accordingly a variant of SAVINASE®.

The present invention also comprises any of the above mentioned subtilases of the invention in combination with any other modification to the amino acid sequence thereof, especially combinations with other modifications known in the art to provide improved properties to the enzyme are envisaged. The art describes a number of subtilase variants with different improved properties and a number of those are mentioned in the "Background of the invention" section. Those references are disclosed here as references to identify a subtilase variant, which advantageously can be combined with a subtilase variant of the invention.

Such combinations comprise positions: 222 (improve oxidation stability), 218 (improves thermal stability), substitutions in the Ca-binding sites stabilizing the enzyme, e.g. position 76, and many other apparent from the prior art.

In another embodiment, a subtilase variant of the invention may advantageously be combined with one or more modification(s) in any of the positions:

27, 36, 57, 76, 87, 97, 101, 104, 120, 123, 167, 170, 206, 218, 222, 224, 235 and 274.

Specifically the following BLSAVI, BLSUBL, BSKSMK, and BAALKP variants are considered appropriate for combination:

K27R, *36D, S57P, N76D, S87N, G97N, S101G, S103A, V104A, V104I, V104N, V104Y, H120D, N123S, Y167, R170, Q206E, N218S, M222S, M222A, T224S, K235L and T274A.

Furthermore variants comprising any of the variants K27R+V104Y+N123S+T274A, N76D+S103A+V104I, N76D+V104A, S87N+S101G+V104N, or S101G+V104N, other combinations of these mutations (K27R, N76D, S101G, V104A, V104N, V104Y, N123S, T274A) in combination with any one or more of the modification(s) mentioned above exhibit improved properties.

Even further subtilase variants of the main aspect(s) of the invention are preferably combined with one or more modification(s) in any of the positions 129, 131, 133 and 194, preferably as 129K, 131H, 133P, 133D and 194P modifications, and most preferably as P129K, P131H, A133P, A133D and A194P modifications. Any of those modification(s) are expected to provide a higher expression level of a subtilase variant of the invention in the production thereof.

Producing a Subtilase Variant

Many methods for cloning a subtilase of the invention and for introducing insertions into genes (e.g. subtilase genes) are well known in the art, cf. the references cited in the "BACKGROUND OF THE INVENTION" section.

In general standard procedures for cloning of genes and introducing insertions (random and/or site directed) into said genes may be used in order to obtain a subtilase variant of the invention. For further description of suitable techniques reference is made to the Examples and Sambrook et al. (1989) Molecular Cloning: A Laboratory Manual, Cold Spring Harbor Lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990); and WO 96/34946.

Further a subtilase variant of the invention may be constructed by standard techniques for artificial creation of diversity, such as by DNA shuffling of different subtilase genes (WO 95/22625; Stemmer WPC, Nature, 370, 389–91 (1994)). DNA shuffling of e.g. the gene encoding SAVINASE® with one or more partial subtilase sequences identified in nature to comprise an active site loop (c) region longer than the active site loop (c) region of SAVINASE®, will after subsequent screening for improved wash performance variants, provide subtilase variants according to the invention.

Expression Vectors

A recombinant expression vector comprising a DNA construct encoding the enzyme of the invention may be any vector which may conveniently be subjected to recombinant DNA procedures.

The choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one that on introduction into a host cell is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gene, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as is a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cell

The DNA sequence encoding the present enzyme introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell which is capable of producing the present enzyme and includes bacteria, yeast, fungi and higher eukaryotic cells including plants.

Examples of bacterial host cells which, on cultivation, are capable of producing the enzyme of the invention are gram-positive bacteria such as strains of Bacillus, such as strains or *B. alkalophilus, B. amyloliquefaciens, B. brevis, B. circulans, B. coagulans, B. lautus, B. lentus, B. licheniformis, B. megaterium, B. stearothermophilus, B. subtilis,* or *B. thuringiensis,* or strains of Streptomyces, such as *S. lividans* or *S. murinus,* or gram-negative bacteria such as *Echerichia coli.*

The transformation of the bacteria may be effected by protoplast transformation, electroporation, conjugation, or by using competent cells in a manner known per se (cf. Sambrook et al., supra).

When expressing the enzyme in bacteria such as *E. coli,* the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as Bacillus or Streptomyces strains, the enzyme may be retained in the cytoplasm, or may be directed to the extracellular medium by a bacterial secretion sequence. In the latter case, the enzyme may be recovered from the medium as described below.

Method of Producing Subtilase

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention.

Thereby it is possible to make a highly purified subtilase composition, characterized in being free from homologous impurities.

In this context, homologous impurities mean any impurities (e.g. other polypeptides than the enzyme of the invention) which originate from the homologous cell where the enzyme of the invention is originally obtained from.

The medium used to culture the transformed host cells may be any conventional medium suitable for growing the host cells in question. The expressed subtilase may conveniently be secreted into the culture medium and may be recovered therefrom by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Use of a Subtilase Variant of the Invention

A subtilase protease variant of the invention may be used for a number of industrial applications, in particular within the detergent industry.

Further the invention relates to an enzyme composition, which comprises a subtilase variant of the invention.

A summary of preferred industrial applications and corresponding preferred enzyme compositions is provided below.

This summary is not in any way intended to be a complete list of suitable applications of subtilase variants of the invention. A subtilase variant of the invention may be used in other industrial applications known in the art for proteases, in particular subtilases.

Detergent Compositions Comprising the Mutant Enzymes

The present invention also relates to the use of the enzymes of the invention in cleaning and detergent compositions and compositions comprising the subtilisin enzymes. Such cleaning and detergent compositions are well described in the art, e.g., in WO 96/34946; WO 97/07202; and WO 95/30011.

Furthermore the example(s) below demonstrate the improvements in wash performance for a number of subtilase variants of the invention.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as an amylase, an arabinase, a carbohydrase, a cellulase, a cutinase, a galactanase, a lipase, a mannanase, an oxidase, e.g., a laccase and/or a peroxidase, a pectinase, a protease, or a xylanase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279).

Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, SAVINASE™, Primase™, Duralase™, Esperase™, and Kannase™ (Novo Nordisk A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from Humicola (synonym Thermomyces), e.g. from *H. lanuginosa* (*T. lanuginosus*) as described in EP 258 068 and EP 305 216 or from *H. insolens* as described in WO 96/13580, a Pseudomonas lipase, e.g. from *P. alcaligenes* or *P. pseudoalcaligenes* (EP 218 272), *P. cepacia* (EP 331 376), *P. stutzeri* (GB 1,372,034), *P. fluorescens*, Pseudomonas sp. strain SD 705 (WO 95/06720 and WO 96/27002), *P. wisconsinensis* (WO 96/12012), a Bacillus lipase, e.g. from *B. subtilis* (Dartois et al. (1993), Biochemica et Biophysica Acta, 1131, 253–360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novo Nordisk A/S).

Amylases: Suitable amylases (alpha and/or beta) include those of bacterial or fungal origin. Chemically modified or protein engineered mutants are included. Amylases include, for example, alpha-amylases obtained from Bacillus, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novo Nordisk A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera Acremonium, Bacillus, Humicola, Fusarium, Pseudomonas, or Thielavia, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, and Carezyme™ (Novo Nordisk A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g. from *C. cinereus*, and variants thereof as those described in WO 93/24618, WO 95/10602, and WO 98/15257.

Commercially available peroxidases include Guardzyme™ (Novo Nordisk A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0–65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly (vinylpyrrolidone), poly (ethylene glycol), poly(vinyl alcohol), poly(vinylpyridine-N-oxide), poly (vinylimidazole), polycarboxylates such as polyacrylates, maleic/acrylic acid copolymers and lauryl methacrylate/acrylic acid copolymers.

The detergent may contain a bleaching system that may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01–100 mg of enzyme protein per liter of wash liquor, preferably 0.05–5 mg of enzyme protein per liter of wash liquor, in particular 0.1–1 mg of enzyme protein per liter of wash liquor.

The enzyme of the invention may additionally be incorporated in the detergent formulations disclosed in WO 97/07202 which is hereby incorporated as reference.

Leather Industry Applications

A subtilase of the invention may be used in the leather industry, in particular for use in depilation of skins.

In said application a subtilase variant of the invention is preferably used in an enzyme composition which further comprises another protease.

For a more detailed description of suitable other proteases see section relating to suitable enzymes for use in a detergent composition (vide supra).

Wool Industry Applications

A subtilase of the invention may be used in the wool industry, in particular for use in cleaning of clothes comprising wool.

In said application a subtilase variant of the invention is preferably used in an enzyme composition which further comprises another protease.

For a more detailed description of suitable other proteases see section relating to suitable enzymes for use in a detergent composition (vide supra).

The invention is described in further detail in the following 15 examples which are not in any way intended to limit the scope of the invention as claimed.

Materials and Methods

Strains:

B. subtilis DN1885 (Diderichsen et al., 1990).

B. lentus 309 and 147 are specific strains of Bacillus lentus, deposited with the NCIB and accorded the accession numbers NCIB 10309 and 10147, and described in U.S. Pat. No. 3,723,250, which is incorporated herein by reference.

E. coli MC 1000 (M. J. Casadaban and S. N. Cohen (1980); J. Mol. Biol. 138 179–207), was made $r^-,m^+$ by conventional methods and is also described in U.S. patent application Ser. No. 039,298.

Plasmids:

pJS3: E. coli-B. subtilis shuttle vector containing a synthetic gene encoding for subtilase 309. (Described by Jacob Schiødt et al. in Protein and Peptide letters 3:39–44 (1996)).

pSX222: B. subtilis expression vector (Described in WO 96/34946).

General Molecular Biology Methods:

Unless otherwise mentioned the DNA manipulations and transformations were performed using standard methods of molecular biology (Sambrook et al. (1989) Molecular cloning: A Laboratory Manual, Cold Spring Harbor Lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

Enzymes for DNA Manipulations

Unless otherwise mentioned all enzymes for DNA manipulations, such as e.g. restiction endonucleases, ligases etc., are obtained from New England Biolabs, Inc.

Proteolytic Activity

In the context of this invention proteolytic activity is expressed in Kilo NOVO Protease Units (KNPU). The activity is determined relative to an enzyme standard (SAVINASE®), and the determination is based on the digestion of a dimethyl casein (DMC) solution by the proteolytic enzyme at standard conditions, i.e. 50° C., pH 8.3, 9 min. reaction time, 3 min. measuring time. A folder AF 220/1 is available upon request to Novo Nordisk A/S, Denmark, which folder is hereby incorporated by reference.

A GU is a Glycine Unit, defined as the proteolytic enzyme activity which, under standard conditions, during a 15 minute incubation at 40° C., with N-acetyl casein as substrate, produces an amount of $NH_2$-group equivalent to 1 mmole of glycine.

Protease activity can also be measured using the PNA assay, with succinyl-alanine-alanine-proline-phenylalanine-paranitrophenol as the substrate. The PNA assay is further described in Rothgeb, T. M., Goodlander, B. D., Garrison, P. H., and Smith, L. A., Journal of American Oil Chemists' Society (1988).

Fermentation:

Fermentations for the production of subtilase enzymes were performed at 30° C. on a rotary shaking table (300 r.p.m.) in 500 ml baffled Erlenmeyer flasks containing 100 ml BPX medium for 5 days.

Consequently in order to make an e.g. 2 liter broth 20 Erlenmeyer flasks were fermented simultaneously.

Media:

| BPX Medium Composition (per liter) | |
| --- | --- |
| Potato starch | 100 g |
| Ground barley | 50 g |
| Soybean flour | 20 g |
| $Na_2HPO_4 \times 12\ H_2O$ | 9 g |
| Pluronic | 0.1 g |
| Sodium caseinate | 10 g |

The starch in the medium is liquefied with alpha-amylase and the medium is sterilized by heating at 120° C. for 45 minutes. After sterilization the pH of the medium is adjusted to 9 by addition of NaHCO$_3$ to 0.1 M.

EXAMPLE 1

Construction and Expression of Enzyme Variants
Site-Directed Mutagenesis:

Subtilase 309 site-directed variants of the invention comprising specific insertions in the active site loop (c) region were made by traditional cloning of DNA fragments (Sambrook et al., Molecular Cloning: A Laboratory Manual, 2nd Ed., Cold Spring Harbor, 1989) produced by PCR of oligos containing the desired insertions (see below).

The template plasmid DNA was pJS3, or an analogue of this containing a variant of subtilase 309.

Insertions were introduced by oligo directed mutagenesis to construct DNA sequences encoding subtilase 309 variants.

DNA encoding subtilase 309 variants was transformed into E. coli. DNA purified from an overnight culture of these transformants was transformed into B. subtilis by restriction endonuclease digestion, purification of DNA fragments, ligation, transformation of B. subtilis. Transformation of B. subtilis was performed as described by Dubnau et al., J. Mol. Biol., 56, 209–221 (1971).

Localized Random Mutagenesis in Order to Insert Random Insertions in a Localized Region:

The overall strategy used to perform localized random mutagenesis was:

A mutagenic primer (oligonucleotide) corresponding to the DNA sequence flanking the site of insertion, separated by the DNA base pairs defining the insertion, was synthesized.

Subsequently, the resulting mutagenic primer was used in a PCR reaction with a suitable opposite primer. The resulting PCR fragment was purified and digested by endonucleases and cloned into the E. coli-B. subtilis shuttle vector (see below).

Following this strategy a localized random library was constructed in SAVINASE wherein insertions were introduced in the active site loop region.

The mutations were introduced by mutagenic primers, so that all amino acids were represented (N=25% of A, T, C, and G; whereas S=50% C and G.

For insertions between positions 125 and 126, the mutagenic primer 5'-C AGC TTG CTC GAG TGT GGC ACT TGG CGA AGG GCT TCC TAA SNN ACT CAA ATT AGC AAC GTG CAT G-3' (anti-sense) (SEQ ID NO: 7) containing the Xho I site in pJS3 was used in a PCR reaction with a suitable sense opposite primer, situated upstream the Hind III site in pJS3 (e.g. 5'-GTT GCT GTC CTC GAT ACA GGG ATA TCC ACT CAT CCA GAT CT-3' (sense) (SEQ ID NO: 8)) with the plasmid pJS3 as template. For insertions between positions 126 and 127, the mutagenic primer 5'-C AGC TTG CTC GAG TGT GGC ACT TGG CGA AGG GCT TCC SNN TAA ACT CAA ATT AGC AAC GTG CAT G-3' (anti-sense) (SEQ ID NO: 9) containing the Xho I site in pJS3 was used in a PCR reaction with a suitable sense opposite primer, situated upstream the Hind III site in pJS3 (e.g. 5'-GTT GCT GTC CTC GAT ACA GGG ATA TCC ACT CAT CCA GAT CT-3' (sense) (SEQ ID NO: 10)) with the plasmid pJS3 as template. For insertions between positions 127 and 128, the mutagenic primer 5'-C AGC TTG CTC GAG TGT GGC ACT TGG CGA AGG GCT SNN TCC TAA ACT CAA ATT AGC AAC GTG CAT G-3' (anti-sense) (SEQ ID NO: 11) containing the Xho I site in pJS3 was used in a PCR reaction with a suitable opposite primer, situated upstream the Hind III site in pJS3 (e.g. 5'-GTT GCT GTC CTC GAT ACA GGG ATA TCC ACT CAT CCA GAT CT-3' (sense) (SEQ ID NO: 12)) with the plasmid pJS3 as template. For insertions between positions 128 and 129, the mutagenic primer 5'-C AGC TTG CTC GAG TGT GGC ACT TGG CGA AGG SNN GCT TCC TAA ACT CAA ATT AGC AAC GTG CAT G-3' (anti-sense) (SEQ ID NO: 13) containing the Xho I site in pJS3 was used in a PCR reaction with a suitable sense opposite primer, situated upstream the Hind III site in pJS3 (e.g. 5'-GTT GCT GTC CTC GAT ACA GGG ATA TCC ACT CAT CCA GAT CT-3' (sense) (SEQ ID NO: 14)) with the plasmid pJS3 as template. For insertions between positions 129 and 130, the mutagenic primer 5'-C AGC TTG CTC GAG TGT GGC ACT TGG CGA SNN AGG GCT TCC TAA ACT CAA ATT AGC AAC GTG CAT G-3' (anti-sense) (SEQ ID NO: 15) containing the Xho I site in pJS3 was used in a PCR reaction with a suitable sense opposite primer, situated upstream the Hind III site in pJS3 (e.g. 5'-GTT GCT GTC CTC GAT ACA GGG ATA TCC ACT CAT CCA GAT CT-3' (sense) (SEQ ID NO: 16)) with the plasmid pJS3 as template. For insertions between positions 130 and 131, the mutagenic primer 5'-C AGC TTG CTC GAG TGT GGC ACT TGG SNN CGA AGG GCT TCC TAA ACT CAA ATT AGC AAC GTG CAT G-3' (anti-sense) (SEQ ID NO: 17) containing the Xho I site in pJS3 was used in a PCR reaction with a suitable sense opposite primer, situated upstream the Hind III site in pJS3 (e.g. 5'-GTT GCT GTC CTC GAT ACA GGG ATA TCC ACT CAT CCA GAT CT-3' (sense) (SEQ ID NO: 18)) with the plasmid pJS3 as template. For insertions between positions 131 and 132, the mutagenic primer 5'-C AGC TTG CTC GAG TGT GGC ACT SNN TGG CGA AGG GCT TCC TAA ACT CAA ATT AGC AAC GTG CAT G-3' (anti-sense) (SEQ ID NO: 19) containing the Xho I site in pJS3 was used in a PCR reaction with a suitable sense opposite primer, situated upstream the Hind III site in pJS3 (e.g. 5'-GTT GCT GTC CTC GAT ACA GGG ATA TCC ACT CAT CCA GAT CT-3' (sense) (SEQ ID NO: 20)) with the plasmid pJS3 as template. For insertions between positions 132 and 133, the mutagenic primer 5'-C AGC TTG CTC GAG TGT GGC SNN ACT TGG CGA AGG GCT TCC TAA ACT CAA ATT AGC AAC GTG CAT G-3' (anti-sense) (SEQ ID NO: 21) containing the Xho I site in pJS3 was used in a PCR reaction with a suitable sense opposite primer, situated upstream the Hind III site in pJS3 (e.g. 5'-GTT GCT GTC CTC GAT ACA GGG ATA TCC ACT CAT CCA GAT CT-3' (sense) (SEQ ID NO: 22)) with the plasmid pJS3 as template.

The resulting PCR products were cloned into the pJS3 shuttle vector by using the restriction enzymes Xho I and Hind III.

The random library was transformed into E. coli by well known techniques.

The library prepared contained approximately 100,000 individual clones/library.

Ten randomly chosen colonies were sequenced to confirm the mutations designed.

In order to purify a subtilase variant of the invention, the B. subtilis pJS3 expression plasmid comprising a variant of the invention was transformed into a competent B. subtilis strain and was fermented as described above in a medium containing 10 micrograms/ml Chloramphenicol (CAM).

EXAMPLE 2

Purification of Enzyme Variants

This procedure relates to purification of a two liter scale fermentation for the production of the subtilases of the invention in a Bacillus host cell.

Approximately 1.6 liters of fermentation broth were centrifuged at 5000 rpm for 35 minutes in 1 liter beakers. The supernatants were adjusted to pH 6.5 using 10% acetic acid and filtered on Seitz Supra S100 filter plates.

The filtrates were concentrated to approximately 400 ml using an Amicon CH2A UF unit equipped with an Amicon S1Y10 UF cartridge. The UF concentrate was centrifuged and filtered prior to absorption at room temperature on a Bacitracin affinity column at pH 7. The protease was eluted from the Bacitracin column at room temperature using 25% 2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step were combined and applied to a 750 ml Sephadex G25 column (5 cm dia.) equilibrated with a buffer containing 0.01 dimethylglutaric acid, 0.2 M boric acid and 0.002 M calcium chloride adjusted to pH 6.5.

Fractions with proteolytic activity from the Sephadex G25 column were combined and applied to a 150 ml CM Sepharose CL 6B cation exchange column (5 cm dia.) equilibrated with a buffer containing 0.01 M dimethylglutaric acid, 0.2 M boric acid, and 0.002 M calcium chloride adjusted to pH 6.5.

The protease was eluted using a linear gradient of 0–0.1 M sodium chloride in 2 liters of the same buffer (0–0.2 M sodium chloride in case of subtilisin 147).

In a final purification step protease containing fractions from the CM Sepharose column were combined and concentrated in an Amicon ultrafiltration cell equipped with a GR81PP membrane (from the Danish Sugar Factories Inc.).

By using the techniques of Example 1 for the construction and fermentation, and the above isolation procedure the following subtilisin 309 variants were produced and isolated:

S125ST
S125SS
S125SD
S125SE
S125SP
S125SG
S125SH
S125SI
S125ST + Y167A
S125SA + P129S
S125SSP + P129G
L126LT
L126LS
L126LD
L126LE
L126LP
L126LG
L126LH
L126LI
L126LT + Y167A
L126LA + P129S
G127GT
G127GS
G127GD
G127GE
G127GP
G127GG
G127GH
G127GI
G127GT + Y167A
S106W + G127GS + P129A
G127GS + P129A + S130T
S128ST

-continued

S128SS
S128SD
S128SE
S128SP
S128SG
S128SH
S128SI
S128SA
S128ST + P129S + P131A
S128ST + P129S
S128STT + P129S + S130A + P131T
S128SA + P129S + S130T + S132A
S128SD + P129PR
P129PA
P129PQ
P129PT
P129PS
P129PD
P129PE
P129PP
P129PG
P129PH
P129PI
P129PAS
P129PHG
P129PAH
S130SA
S130ST
S130SS
S130SD
S130SE
S130SP
S130SG
S130SH
S130SI
S130ST + Y167A
P129S + S130SA
P129S + S130TP
P129G + S130SSP
S130SNN + P131H
S130SLA + P131A
S130STT
S130SHQ
P131PA
P131PT
P131PS
P131PD
P131PE
P131PP
P131PG
P131PH
P131PI
G70C + S128A + P129T + S130T + P131STR
S128A + P131PTA
S132SS
S132SD
S132SE
S132SP
S132SG
S132SH
S132SI
S132SA
S132ST
S128T + S130A + P131T + S132STP

These variants were found to exhibit better wash performance than SAVINASE in a preliminary assay.

EXAMPLE 3

Wash Performance of Detergent Compositions Comprising Enzyme Variants

The following examples provide results from a number of washing tests that were conducted under the conditions indicated.

Mini Wash
Wash Conditions:

|  | Europe | Detergent 95 | US |
| --- | --- | --- | --- |
| Detergent Dosage | 4 g/l | 3 g/l | 1 g/l |
| Wash Temp | 30° C. | 15° C. | 25° C. |
| Wash Time | 30 min | 15 min | 10 min |
| Water hardness | 18° dH ($Ca^{2+}/Mg^{2+}$ = 5:1) | 6° dH | 6° dH ($Ca^{2+}/Mg^{2+}$ = 2:1) |
| pH | Not adjusted | 10.5 | Not adjusted |
| Enzyme conc. | 1, 2, 5, 10, 30 nM | | 1, 2, 5, 10, 30 nM |
| Test system | 150 ml glass beakers with a stirring rod | 10 nm | 150 ml glass beakers with a stirring rod |
| Textile/volume | 5 textile pieces (Ø 2.5 cm) in 50 ml detergent | 5 textile pieces (Ø 2.5 cm) in 50 ml detergent | 5 textile pieces (Ø 2.5 cm) in 50 ml detergent |
| Test Material | EMPA116 | EMPA117 | EMPA117 |

Detergents:

The detergents used were obtained from supermarkets in Denmark (OMO, datasheet ED-9745105) and the USA (Wisk, datasheet ED-9711893), respectively. Prior to use, all enzymatic activity in the detergents was inactivated by microwave treatment.

Swatches:

The swatches used were EMPA116 and EMPA117, obtained from EMPA Testmaterialen, Movenstrasse 12, CH-9015 St. Gall, Switzerland.

Reflectance

Measurement of reflectance (R) on the test material was done at 460 nm using a Macbeth ColorEye 7000 photometer. The measurements were done according to the manufacturer's protocol.

Evaluation

The evaluation of the wash performance of a subtilase is determined by either the improvement factor or the performance factor for the subtilase investigated.

The improvement factor, $IF_{Dose/response}$, is defined as the ratio between the slopes of the wash performance curves for a detergent containing the subtilase investigated and the same detergent containing a reference subtilase at the asymptotic concentration of the subtilase goes to zero $$IF_{Dose/response} = a/a_{ref}$$

The wash performance is calculated according to the formula I:

$$R = R_0 + (a\ \text{delta}R_{max}\ c)/(\text{delta}R_{max} + a\ c)$$

where

R is the wash performance in reflectance units; $R_0$ is the intercept of the fitted curve with y-axis (blind); a is the slope of the fitted curve as c→0; c is the enzyme concentration; and $\text{delta}R_{max}$ is the theoretical maximal wash effect as c→∞.

The performance factor, P, is calculated according to formula II $$P = (R_{variant} - R_{blank})/(R_{SAVINASE} - R_{blank}) \quad (ii)$$

where $R_{variant}$ is the reflectance of test material washed with 10 nM variant; $R_{SAVINASE}$ is the reflectance of test material washed with 10 nM SAVINASE; $R_{blank}$ is the reflectance of test material washed with no enzyme.

| Variant | $IF_{Dose/response}$ | P |
| --- | --- | --- |
| US (detergent: OMO, Swatch: EMPA116) | | |
| P129G + S130SSP | — | 1.2 |
| US (detergent: US Wisk, Swatch: EMPA117) | | |
| G127GA | — | 1.4 |
| G127GS + P129A + S130T | — | 1.3 |
| S128SA | — | 1.7 |
| S128SDR | — | 1.2 |
| S128ST + P129S + P131A | — | 1.3 |
| S128ST + P129S | — | 1.3 |
| P129PT | — | 1.3 |
| P129PA | — | 1.7 |
| P129PS | — | 1.3 |
| P129PQ | — | 1.3 |
| P129PAS | — | 1.3 |
| P129PHG | — | 1.2 |
| P129PAH | — | 1.3 |
| S130SA | — | 1.4 |
| S130SST | — | 1.4 |
| S130SHQ | — | 1.4 |
| P129S + S130SA | — | 1.3 |
| P129S + S130TP | — | 1.3 |
| P129G + S130SSP | — | 1.5 |
| S130SNN + P131H | — | 1.3 |
| S130SLA + P131A | — | 1.8 |
| P131PA | — | 1.3 |
| S128A + P131PTA | — | 1.3 |
| S132SA | — | 1.4 |
| S132ST | — | 1.5 |

The results show that subtilases of the inventions exhibit improved wash performance in comparison to SAVINASE®.

What is claimed is:

1. A modified subtilase comprising a mutation in an amino acid sequence of a subtilase, wherein the mutation is an insertion of one or more amino acid residues at position 125 of the active site loop (c) region corresponding to positions 125 to 132, wherein the positions are numbered according to the amino acid sequence of the mature subtilisin BPN' of SEQ ID NO: 4.

2. The modified subtilase of claim 1, wherein the one or more amino acid residues are A, G, S or T.

3. The modified subtilase of claim 1, wherein the one or more amino acid residues are D, E, H, K or R.

4. The modified subtilase of claim 1, wherein the one or more amino acid residues are C, N, Q, S or T.

5. The modified subtilase of claim 1, wherein the one or more amino acid residues are A, G or V.

6. The modified subtilase of claim 1, wherein the one or more amino acid residues are F, I, L, M, P, W or Y.

7. The modified subtilase of claim 1, comprising S125ST+Y167A.

8. The modified subtilase of claim 1, wherein the mutation is an insertion of two or more amino acid residues at position 125.

9. The modified subtilase of claim 1, comprising at least one further mutation at one or more positions.

10. The modified subtilase of claim 9, wherein the one or more positions are selected from the group consisting of 27, 36, 57, 76, 87, 97, 101, 104, 120, 123, 167, 170, 206, 218, 222, 224, 235 and 274.

11. The modified subtilase of claim 10, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

12. The modified subtilase of claim 11, wherein the at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

13. The modified subtilase of claim 9, wherein the one or more positions are selected from the group consisting of 129, 131, 133 and 194.

14. The modified subtilase of claim 13, wherein the at least one further mutation is selected from the group consisting of P129K, P131H, A133D, A133P, and A194P.

15. The modified subtilase of claim 1, wherein the subtilase is a sub-group I-S1 subtilase.

16. The modified subtilase of claim 15, wherein the subtilase is selected from the group consisting of subtilisin I168, subtilisin BPN', subtilisin DY, and subtilisin Carlsberg.

17. The modified subtilase of claim 1, wherein the subtilase is a sub-group I-S2 subtilase.

18. The modified subtilase of claim 17, wherein the subtilase is subtilisin 147, subtilisin 309, subtilisin PB92, and subtilisin YaB.

19. A composition comprising a modified subtilase of claim 1 and a surfactant.

20. The composition of claim 19, further comprising an amylase, cellulase, cutinase, lipase, oxidoreductase, or another protease.

21. An isolated DNA sequence encoding a modified subtilase of claim 1.

22. An expression vector comprising an isolated DNA sequence of claim 21.

23. A microbial host cell transformed with an expression vector of claim 22.

24. A method for producing a modified subtilase, comprising
  (a) culturing a microbial host cell of claim 23 under conditions conducive to the expression and secretion of the modified subtilase, and
  (b) recovering the modified subtilase.

25. A modified subtilase comprising a mutation in an amino acid sequence of a subtilase, wherein the mutation is an insertion of one or more amino acid residues at position 126 of the active site loop (c) region corresponding to positions 125 to 132, wherein the positions are numbered according to the amino acid sequence of the mature subtilisin BPN' of SEQ ID NO: 4.

26. The modified subtilase of claim 25, wherein the one or more amino acid residues are A, G, S or T.

27. The modified subtilase of claim 25, wherein the one or more amino acid residues are D, E, H, K or R.

28. The modified subtilase of claim 25, wherein the one or more amino acid residues are C, N, Q, S or T.

29. The modified subtilase of claim 25, wherein the one or more amino acid residues are A, G or V.

30. The modified subtilase of claim 25, wherein the one or more amino acid residues are F, I, L, M, P, W or Y.

31. The modified subtilase of claim 25, comprising L126LT+Y167A.

32. The modified subtilase of claim 25, wherein the mutation is an insertion of two or more amino acid residues at position 126.

33. The modified subtilase of claim 25, comprising at least one further mutation at one or more positions.

34. The modified subtilase of claim 33, wherein the one or more positions are selected from the group consisting of 27, 36, 57, 76, 87, 97, 101, 104, 120, 123, 167, 170, 206, 218, 222, 224, 235 and 274.

35. The modified subtilase of claim 34, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

36. The modified subtilase of claim 35, wherein the at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

37. The modified subtilase of claim 33, wherein the one or more positions are selected from the group consisting of 129, 131, 133 and 194.

38. The modified subtilase of claim 37, wherein the at least one further mutation is selected from the group consisting of P129K, P131H, A133D, A133P, and A194P.

39. The modified subtilase of claim 25, wherein the subtilase is a sub-group I-S1 subtilase.

40. The modified subtilase of claim 39, wherein the subtilase is selected from the group consisting of subtilisin I168, subtilisin BPN', subtilisin DY, and subtilisin Carlsberg.

41. The modified subtilase of claim 25, wherein the subtilase is a sub-group I-S2 subtilase.

42. The modified subtilase of claim 41, wherein the subtilase is subtilisin 147, subtilisin 309, subtilisin PB92, and subtilisin YaB.

43. A composition comprising a modified subtilase of claim 25 and a surfactant.

44. The composition of claim 43, further comprising an amylase, cellulase, cutinase, lipase, oxidoreductase, or another protease.

45. An isolated DNA sequence encoding a modified subtilase of claim 25.

46. An expression vector comprising an isolated DNA sequence of claim 45.

47. A microbial host cell transformed with an expression vector of claim 46.

48. A method for producing a modified subtilase, comprising
  (a) culturing a microbial host cell of claim 47 under conditions conducive to the expression and secretion of the modified subtilase, and
  (b) recovering the modified subtilase.

49. A modified subtilase comprising a mutation in an amino acid sequence of a subtilase, wherein the mutation is an insertion of one or more amino acid residues at position 127 of the active site loop (c) region corresponding to positions 125 to 132, wherein the positions are numbered according to the amino acid sequence of the mature subtilisin BPN' of SEQ ID NO: 4.

50. The modified subtilase of claim 49, wherein the one or more amino acid residues are A, G, S or T.

51. The modified subtilase of claim 49, wherein the one or more amino acid residues are D, E, H, K or R.

52. The modified subtilase of claim 49, wherein the one or more amino acid residues are C, N, Q, S or T.

53. The modified subtilase of claim 49, wherein the one or more amino acid residues are A, G or V.

54. The modified subtilase of claim 49, wherein the one or more amino acid residues are F, I, L, M, P, W or Y.

55. The modified subtilase of claim 49, comprising

S106W+G127GS+P129A,
G127GA,
G127GS+P129A+S130T, or
G127GT+Y167A.

56. The modified subtilase of claim 49, wherein the mutation is an insertion of two or more amino acid residues at position 127.

57. The modified subtilase of claim 49, comprising at least one further mutation at one or more positions.

58. The modified subtilase of claim 57, wherein the one or more positions are selected from the group consisting of 27, 36, 57, 76, 87, 97, 101, 104, 120, 123, 167, 170, 206, 218, 222, 224, 235 and 274.

59. The modified subtilase of claim 58, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

60. The modified subtilase of claim 59, wherein the at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

61. The modified subtilase of claim 57, wherein the one or more positions are selected from the group consisting of 129, 131, 133 and 194.

62. The modified subtilase of claim 61, wherein the at least one further mutation is selected from the group consisting of P129K, P131H, A133D, A133P, and A194P.

63. The modified subtilase of claim 49, wherein the subtilase is a sub-group I-S1 subtilase.

64. The modified subtilase of claim 63, wherein the subtilase is selected from the group consisting of subtilisin I168, subtilisin BPN', subtilisin DY, and subtilisin Carlsberg.

65. The modified subtilase of claim 49, wherein the subtilase is a sub-group I-S2 subtilase.

66. The modified subtilase of claim 65, wherein the subtilase is subtilisin 147, subtilisin 309, subtilisin PB92, and subtilisin YaB.

67. A composition comprising a modified subtilase of claim 49 and a surfactant.

68. The composition of claim 67, further comprising an amylase, cellulase, cutinase, lipase, oxidoreductase, or another protease.

69. An isolated DNA sequence encoding a modified subtilase of claim 49.

70. An expression vector comprising an isolated DNA sequence of claim 69.

71. A microbial host cell transformed with an expression vector of claim 70.

72. A method for producing a modified subtilase, comprising
   (a) culturing a microbial host cell of claim 71 under conditions conducive to the expression and secretion of the modified subtilase, and
   (b) recovering the modified subtilase.

73. A modified subtilase comprising a mutation in an amino acid sequence of a subtilase, wherein the mutation is an insertion of one or more amino add residues at position 128 of the active site loop (c) region corresponding to positions 125 to 132, wherein the positions are numbered according to the amino acid sequence of the mature subtilisin BPN' of SEQ ID NO: 4.

74. The modified subtilase of claim 73, wherein the one or more amino acid residues are A, G, S or T.

75. The modified subtilase of claim 73, wherein the one or more amino acid residues are D, E, H, K or R.

76. The modified subtilase of claim 73, wherein the one or more amino acid residues are C, N, Q, S or T.

77. The modified subtilase of claim 73, wherein the one or more amino acid residues are A, G or V.

78. The modified subtilase of claim 73, wherein the one or more amino acid residues are F, I, L, M, P, W or Y.

79. The modified subtilase of claim 73, comprising
S128SA,
S128SA+P129S+S130T+S132A,
S128SD+P129PR,
S128ST+P129S,
S128ST+P129S+P131A,
S128ST+Y167A, or
S128STT+P129S+S130A+P131T.

80. The modified subtilase of claim 73, wherein the mutation is an insertion of two or more amino acid residues at position 128.

81. The modified subtilase of claim 73, comprising at least one further mutation at one or more positions.

82. The modified subtilase of claim 81, wherein the one or more positions are selected from the group consisting of 27, 36, 57, 76, 87, 97, 101, 104, 120, 123, 167, 170, 206, 218, 222, 224, 235 and 274.

83. The modified subtilase of claim 82, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

84. The modified subtilase of claim 83, wherein the at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

85. The modified subtilase of claim 81, wherein the one or more positions are selected from the group consisting of 129, 131, 133 and 194.

86. The modified subtilase of claim 85, wherein the at least one further mutation is selected from the group consisting of P129K, P131H, A133D, A133P, and A194P.

87. The modified subtilase of claim 73, wherein the subtilase is a sub-group I-S1 subtilase.

88. The modified subtilase of claim 87, wherein the subtilase is selected from the group consisting of subtilisin I168, subtilisin BPN', subtilisin DY, and subtilisin Carlsberg.

89. The modified subtilase of claim 73, wherein the subtilase is a sub-group I-S2 subtilase.

90. The modified subtilase of claim 89, wherein the subtilase is subtilisin 147, subtilisin 309, subtilisin PB92, and subtilisin YaB.

91. A composition comprising a modified subtilase of claim 73 and a surfactant.

92. The composition of claim 91, further comprising an amylase, cellulase, cutinase, lipase, oxidoreductase, or another protease.

93. An isolated DNA sequence encoding a modified subtilase of claim 73.

94. An expression vector comprising an isolated DNA sequence of claim 93.

95. A microbial host cell transformed with an expression vector of claim 94.

96. A method for producing a modified subtilase, comprising (a) culturing a microbial host cell of claim 95 under conditions conducive to the expression and secretion of the modified subtilase, and (b) recovering the modified subtilase.

97. A modified subtilase comprising a mutation in an amino acid sequence of a subtilase, wherein the mutation is an insertion of one or more amino acid residues at position 129 of the active site loop (c) region corresponding to positions 125 to 132, wherein the positions are numbered according to the amino acid sequence of the mature subtilisin BPN' of SEQ ID NO: 4.

98. The modified subtilase of claim 97, wherein the one or more amino acid residues are A, G, S or T.

99. The modified subtilase of claim 97, wherein the one or more amino acid residues are D, E, H, K or R.

100. The modified subtilase of claim 97, wherein the one or more amino acid residues are C, N, Q, S or T.

101. The modified subtilase of claim 97, wherein the one or more amino acid residues are A, G or V.

102. The modified subtilase of claim 97, wherein the one or more amino acid residues are F, I, L, M, P, W or Y.

103. The modified subtilase of claim 97, comprising

S128SD+P129PR,

P129PA,

P129PAH,

P129PAS,

P129PHG,

P129PQ,

P129PS,

P129PT, or

P129PT+Y167A.

104. The modified subtilase of claim 97, wherein the mutation is an insertion of two or more amino acid residues at position 129.

105. The modified subtilase of claim 97, comprising at least one further mutation at one or more positions.

106. The modified subtilase of claim 105, wherein the one or more positions are selected from the group consisting of 27, 36, 57, 76, 87, 97, 101, 104, 120, 123, 167, 170, 206, 218, 222, 224, 235 and 274.

107. The modified subtilase of claim 106, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

108. The modified subtilase of claim 107, wherein the at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

109. The modified subtilase of claim 105, wherein the one or more positions are selected from the group consisting of 129, 131, 133 and 194.

110. The modified subtilase of claim 109, wherein the at least one further mutation is selected from the group consisting of P129K, P131H, A133D, A133P, and A194P.

111. The modified subtilase of claim 97, wherein the subtilase is a sub-group I-S1 subtilase.

112. The modified subtilase of claim 111, wherein the subtilase is selected from the group consisting of subtilisin I168, subtilisin BPN', subtilisin DY, and subtilisin Carlsberg.

113. The modified subtilase of claim 97, wherein the subtilase is a sub-group I-S2 subtilase.

114. The modified subtilase of claim 113, wherein the subtilase is subtilisin 147, subtilisin 309, subtilisin PB92, and subtilisin YaB.

115. A composition comprising a modified subtilase of claim 97 and a surfactant.

116. The composition of claim 115, further comprising an amylase, cellulase, cutinase, lipase, oxidoreductase, or another protease.

117. An isolated DNA sequence encoding a modified subtilase of claim 97.

118. An expression vector comprising an isolated DNA sequence of claim 117.

119. A microbial host cell transformed with an expression vector of claim 118.

120. A method for producing a modified subtilase, comprising (a) culturing a microbial host cell of claim 119 under conditions conducive to the expression and secretion of the modified subtilase, and (b) recovering the modified subtilase.

121. A modified subtilase comprising a mutation in an amino acid sequence of a subtilase, wherein the mutation is an insertion of one or more amino acid residues at position 130 of the active site loop (c) region corresponding to positions 125 to 132, wherein the positions are numbered according to the amino acid sequence of the mature subtilisin BPN' of SEQ ID NO: 4.

122. The modified subtilase of claim 121, wherein the one or more amino acid residues are A, G, S or T.

123. The modified subtilase of claim 121, wherein the one or more amino acid residues are D, E, H K or R.

124. The modified subtilase of claim 121, wherein the one or more amino acid residues are C, N, Q, S or T.

125. The modified subtilase of claim 121, wherein the one or more amino acid residues are A, G or V.

126. The modified subtilase of claim 121, wherein the one or more amino acid residues are F, I, L, M, P, W or Y.

127. The modified subtilase of claim 121, comprising

P129G+S130SP,

P129G+S130SSP,

P129S+S130SA,

P129S+S130TP,

S130SA,

S130SHQ,

S130SLA+P131A,

S130SNN+P131H,

S130ST+Y167A, or

S130STT.

128. The modified subtilase of claim 121, wherein the mutation is an insertion of two or more amino acid residues at position 130.

129. The modified subtilase of claim 121, comprising at least one further mutation at one or more positions.

130. The modified subtilase of claim 129, wherein the one or more positions are selected from the group consisting of 27, 36, 57, 76, 87, 97, 101, 104, 120, 123, 167, 170, 206, 218, 222, 224, 235 and 274.

131. The modified subtilase of claim 130, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

132. The modified subtilase of claim 131, wherein the at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

133. The modified subtilase of claim 129, wherein the one or more positions are selected from the group consisting of 129, 131, 133 and 194.

134. The modified subtilase of claim 133, wherein the at least one further mutation is selected from the group consisting of P129K, P131H, A133D, A133P, and A194P.

135. The modified subtilase of claim 121, wherein the subtilase is a sub-group I-S1 subtilase.

136. The modified subtilase of claim 135, wherein the subtilase is selected from the group consisting of subtilisin I168, subtilisin BPN', subtilisin DY, and subtilisin Carlsberg.

137. The modified subtilase of claim 121, wherein the subtilase is a sub-group I-S2 subtilase.

138. The modified subtilase of claim 137, wherein the subtilase is subtilisin 147, subtilisin 309, subtilisin PB92, and subtilisin YaB.

139. A composition comprising a modified subtilase of claim 121 and a surfactant.

140. The composition of claim 139, further comprising an amylase, cellulase, cutinase, lipase, oxidoreductase, or another protease.

141. An isolated DNA sequence encoding a modified subtilase of claim 121.

142. An expression vector comprising an isolated DNA sequence of claim 141.

143. A microbial host cell transformed with an expression vector of claim 142.

144. A method for producing a modified subtilase, comprising
    (a) culturing a microbial host cell of claim 143 under conditions conducive to the expression and secretion of the modified subtilase, and
    (b) recovering the modified subtilase.

145. A modified subtilase comprising a mutation in an amino acid sequence of a subtilase, wherein the mutation is an insertion of one or more additional amino add residues at position 131 of the active site loop (c) region corresponding to positions 125 to 132, wherein the positions are numbered according to the amino add sequence of the mature subtilisin BPN' of SEQ ID NO: 4.

146. The modified subtilase of claim 145, wherein the one or more amino acid residues are A, G, S or T.

147. The modified subtilase of claim 145, wherein the one or more amino acid residues are D, E, H, K or R.

148. The modified subtilase of claim 145, wherein the one or more amino acid residues are C, N, Q, S or T.

149. The modified subtilase of claim 145, wherein the one or more amino acid residues are A, G or V.

150. The modified subtilase of claim 145, wherein the one or more amino acid residues are F, I, L, M, P, W or Y.

151. The modified subtilase of claim 145, comprising
    G70C+S128A+P129T+S130T+P131STR,
    S128A+P131PTA,
    P131PA, or
    P131PT+Y167A.

152. The modified subtilase of claim 145, wherein the mutation is an insertion of two or more amino acid residues at position 131.

153. The modified subtilase of claim 145, comprising at least one further mutation at one or more positions.

154. The modified subtilase of claim 153, wherein the one or more positions are selected from the group consisting of 27, 36, 57, 76, 87, 97, 101, 104, 120, 123, 167, 170, 206, 218, 222, 224, 235 and 274.

155. The modified subtilase of claim 154, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

156. The modified subtilase of claim 155, wherein the at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

157. The modified subtilase of claim 153, wherein the one or more positions are selected from the group consisting of 129, 131, 133 and 194.

158. The modified subtilase of claim 157, wherein the at least one further mutation is selected from the group consisting of P129K, P131H, A133D, A133P, and A194P.

159. The modified subtilase of claim 145, wherein the subtilase is a sub-group I-S1 subtilase.

160. The modified subtilase of claim 159, wherein the subtilase is selected from the group consisting of subtilisin I168, subtilisin BPN', subtilisin DY, and subtilisin Carlsberg.

161. The modified subtilase of claim 145, wherein the subtilase is a sub-group I-S2 subtilase.

162. The modified subtilase of claim 161, wherein the subtilase is subtilisin 147, subtilisin 309, subtilisin PB92, and subtilisin YaB.

163. A composition comprising a modified subtilase of claim 145 and a surfactant.

164. The composition of claim 163, further comprising an amylase, cellulase, cutinase, lipase, oxidoreductase, or another protease.

165. An isolated DNA sequence encoding a modified subtilase of claim 145.

166. An expression vector comprising an isolated DNA sequence of claim 165.

167. A microbial host cell transformed with an expression vector of claim 166.

168. A method for producing a modified subtilase, comprising
    (a) culturing a microbial host cell of claim 167 under conditions conducive to the expression and secretion of the modified subtilase, and
    (b) recovering the modified subtilase.

169. A modified subtilase comprising a mutation in an amino acid sequence of a subtilase, wherein the mutation is an insertion of one or more amino acid residues at position 132 of the active site loop (c) region corresponding to positions 125 to 132, wherein the positions are numbered according to the amino acid sequence of the mature subtilisin BPN' of SEQ ID NO: 4.

170. The modified subtilase of claim 169, wherein the one or more amino acid residues are A, G, S or T.

171. The modified subtilase of claim 169, wherein the one or more amino acid residues are D, E, H, K or R.

172. The modified subtilase of claim 169, wherein the one or more amino acid residues are C, N, Q, S or T.

173. The modified subtilase of claim 169, wherein the one or more amino acid residues are A, G or V.

174. The modified subtilase of claim 169, wherein the one or more amino acid residues are F, I, L, M, P, W or Y.

175. The modified subtilase of claim 169, comprising
    S128T+S130A+P131T+S132STP,
    S132SA, S132ST, or
S132ST+Y167A.

176. The modified subtilase of claim 169, wherein the mutation is an insertion of two or more amino acid residues at position 132.

177. The modified subtilase of claim 169, comprising at least one further mutation at one or more positions.

178. The modified subtilase of claim 177, wherein the one or more positions are selected from the group consisting of 27, 36, 57, 76, 87, 97, 101, 104, 120, 123, 167, 170, 206, 218, 222, 224, 235 and 274.

179. The modified subtilase of claim 178, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

180. The modified subtilase of claim 179, wherein the at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

181. The modified subtilase of claim 177, wherein the one or more positions are selected from the group consisting of 129, 131, 133 and 194.

182. The modified subtilase of claim 181, wherein the at least one further mutation is selected from the group consisting of P129K, P131H, A133D, A133P, and A194P.

183. The modified subtilase of claim 169, wherein the subtilase is a sub-group I-S1 subtilase.

184. The modified subtilase of claim 183, wherein the subtilase is selected from the group consisting of subtilisin I168, subtilisin BPN', subtilisin DY, and subtilisin Carlsberg.

185. The modified subtilase of claim 169, wherein the subtilase is a sub-group I-S2 subtilase.

186. The modified subtilase of claim 185, wherein the subtilase is subtilisin 147, subtilisin 309, subtilisin PB92, and subtilisin YaB.

187. A composition comprising a modified subtilase of claim 169 and a surfactant.

188. The composition of claim 187, further comprising an amylase, cellulase, cutinase, lipase, oxidoreductase, or another protease.

189. An isolated DNA sequence encoding a modified subtilase of claim 169.

190. An expression vector comprising an isolated DNA sequence of claim 189.

191. A microbial host cell transformed with an expression vector of claim 190.

192. A method for producing a modified subtilase, comprising
(a) culturing a microbial host cell of claim 191 under conditions conducive to the expression and secretion of the modified subtilase, and
(b) recovering the modified subtilase.

193. The modified subtilase of claim 1, wherein the mutation comprises: S125SA, S125SC, S125SD, S125SE, S125SF, S125SG, S125SH, S125SI, S125SK, S125SL, S125SM. S125SN, S125SP, S125SQ, S125SR, S125SS, S125ST, S125SV, S125SW, or S125SY.

194. The modified subtilase of claim 25, wherein the mutation comprises: L126LA, L126LC, L126LD, L126LE, L126LF, L126LH, L126LI, L126LK, L126LL, L126LM, L126LN, L126LP, L126LQ, L126LR, L126LS, L126LT, L126LV, L126LW, or L126LY.

195. The modified subtilase of claim 49, wherein the mutation comprises: G127GA, G127GC, G127GD, G127GE, G127GF, G127GG, G127GH, G127GI, G127GK, G127GL, G127GM, G127GN, G127GP, G127GQ, G127GR, G127GS, G127GT, G127GV, G127GW, or G127GY.

196. The modified subtilase of claim 73, wherein the mutation comprises: S128SA, S128SC, S128SD, S128SE, S128SF, S128SG, S128SH, S128SI, S128SK, S128SL, S128SM, S128SN, S128SP, S128SQ, S128SR, S128SS, S128ST, S128SV, S128SW, or S128SY.

197. The modified subtilase of claim 97, wherein the mutation comprises: P129PA, P129PC, P129PD, P129PE, P129PF, P129PG, P129PH, P129PI, P129PK, P129PL, P129PM, P129PN, P129PP, P129PQ, P129PR, P129PS, P129PT, P129PV, P129PW, or P129PY.

198. The modified subtilase of claim 121, wherein the mutation comprises: S130SA, S130SC, S130SD, S130SE, S130SF, S130SG, S130SH, S130SI, S130SK, S130SL, S130SM, S130SN, S130SP, S130SQ, S130SR, S130SS, S130ST, S130SV, S130SW, or S130SY.

199. The modified subtilase of claim 145, wherein the mutation comprises: P131PA, P131PC, P131PD, P131PE, P131PF, P131PG, P131PH, P131PI, P131PK, P131PL, P131PM, P131PN, P131PP, P131PQ, P131PR, P131PS, P131PT, P131PV, P131PW, or P131PY.

200. The modified subtilase of claim 169, wherein the mutation comprises: S132SA, S132SC, S132SD, S132SE, S132SF, S132SG, S132SH, S132SI, S132SK, S132SL, S132SM, S132SN, S132SP, S132SQ, S132SR, S132SS, S132ST, S132SV, S132SW, or S132SY.

* * * * *

SEQUENCE LISTING

<160> NUMBER OF SEQ ID NOS: 38

<210> SEQ ID NO 1
<211> LENGTH: 3
<212> TYPE: PRT
<213> ORGANISM: Artificial Sequence
<220> FEATURE:
<223> OTHER INFORMATION: Synthetic

<400> SEQUENCE: 1

Ala Gly Leu
1

<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2

Ala Gly Lys Ala Ser Leu
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

Ala Gly Gly Leu
1

<210> SEQ ID NO 4
<211> LENGTH: 275
<212> TYPE: PRT
<213> ORGANISM: Bacillus

<400> SEQUENCE: 4

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly

```
                145                 150                 155                 160
Ser Ser Ser Thr Val Gly Tyr Pro Gly Lys Tyr Pro Ser Val Ile Ala
                    165                 170                 175
Val Gly Ala Val Asp Ser Ser Asn Gln Arg Ala Ser Phe Ser Ser Val
            180                 185                 190
Gly Pro Glu Leu Asp Val Met Ala Pro Gly Val Ser Ile Gln Ser Thr
            195                 200                 205
Leu Pro Gly Asn Lys Tyr Gly Ala Tyr Asn Gly Thr Ser Met Ala Ser
        210                 215                 220
Pro His Val Ala Gly Ala Ala Ala Leu Ile Leu Ser Lys His Pro Asn
225                 230                 235                 240
Trp Thr Asn Thr Gln Val Arg Ser Ser Leu Glu Asn Thr Thr Thr Lys
                245                 250                 255
Leu Gly Asp Ser Phe Tyr Tyr Gly Lys Gly Leu Ile Asn Val Gln Ala
                260                 265                 270
Ala Ala Gln
        275

<210> SEQ ID NO 5
<211> LENGTH: 269
<212> TYPE: PRT
<213> ORGANISM: Bacillus

<400> SEQUENCE: 5

Ala Gln Ser Val Pro Trp Gly Ile Ser Arg Val Gln Ala Pro Ala Ala
1               5                   10                  15
His Asn Arg Gly Leu Thr Gly Ser Gly Val Lys Val Ala Val Leu Asp
                20                  25                  30
Thr Gly Ile Ser Thr His Pro Asp Leu Asn Ile Arg Gly Gly Ala Ser
            35                  40                  45
Phe Val Pro Gly Glu Pro Ser Thr Gln Asp Gly Asn Gly His Gly Thr
        50                  55                  60
His Val Ala Gly Thr Ile Ala Ala Leu Asn Asn Ser Ile Gly Val Leu
65                  70                  75                  80
Gly Val Ala Pro Ser Ala Glu Leu Tyr Ala Val Lys Val Leu Gly Ala
                85                  90                  95
Ser Gly Ser Gly Ser Val Ser Ser Ile Ala Gln Gly Leu Glu Trp Ala
                100                 105                 110
Gly Asn Asn Gly Met His Val Ala Asn Leu Ser Leu Gly Ser Pro Ser
            115                 120                 125
Pro Ser Ala Thr Leu Glu Gln Ala Val Asn Ser Ala Thr Ser Arg Gly
        130                 135                 140
Val Leu Val Val Ala Ala Ser Gly Asn Ser Gly Ala Gly Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
            180                 185                 190
Val Ala Pro Gly Val Asn Val Gln Ser Thr Tyr Pro Gly Ser Thr Tyr
        195                 200                 205
Ala Ser Leu Asn Gly Thr Ser Met Ala Thr Pro His Val Ala Gly Ala
        210                 215                 220
Ala Ala Leu Val Lys Gln Lys Asn Pro Ser Trp Ser Asn Val Gln Ile
225                 230                 235                 240
```

```
Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 6
<211> LENGTH: 274
<212> TYPE: PRT
<213> ORGANISM: Bacillus

<400> SEQUENCE: 6

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Thr Tyr Ser Gly Ile Val Ser Gly Ile Glu Trp
            100                 105                 110

Ala Thr Thr Asn Gly Met Asp Val Ile Asn Met Ser Leu Gly Gly Pro
        115                 120                 125

Ser Gly Ser Thr Ala Met Lys Gln Ala Val Asp Asn Ala Tyr Ala Arg
    130                 135                 140

Gly Val Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Ser Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 7
<211> LENGTH: 65
<212> TYPE: DNA
<213> ORGANISM: Artificial Sequence
<220> FEATURE:
<223> OTHER INFORMATION: Primer
<220> FEATURE:
<221> NAME/KEY: Misc_feature
<222> LOCATION: (42)..(42)
<223> OTHER INFORMATION: n denotes any nucleotide
<220> FEATURE:
```

```
<221> NAME/KEY: Misc_feature
<222> LOCATION: (43)..(43)
<223> OTHER INFORMATION: n denotes any nucleotide

<400> SEQUENCE: 7
cagcttgctc gagtgtggca cttggcgaag ggcttcctaa snnactcaaa ttagcaacgt    60
gcatg                                                               65

<210> SEQ ID NO 8
<211> LENGTH: 41
<212> TYPE: DNA
<213> ORGANISM: Artificial Sequence
<220> FEATURE:
<223> OTHER INFORMATION: Primer

<400> SEQUENCE: 8
gttgctgtcc tcgatacagg gatatccact catccagatc t                       41

<210> SEQ ID NO 9
<211> LENGTH: 65
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (39)..(39)
<223> OTHER INFORMATION: n denotes any nucleotide
<220> FEATURE:
<221> NAME/KEY: misc_feature
<222> LOCATION: (40)..(40)
<223> OTHER INFORMATION: n denotes any nucleotide

<400> SEQUENCE: 9
cagcttgctc gagtgtggca cttggcgaag ggcttccsnn taaactcaaa ttagcaacgt    60
gcatg                                                               65

<210> SEQ ID NO 10
<211> LENGTH: 41
<212> TYPE: DNA
<213> ORGANISM: Artificial Sequence
<220> FEATURE:
<223> OTHER INFORMATION: Primer

<400> SEQUENCE: 10
gttgctgtcc tcgatacagg gatatccact catccagatc t                       41

<210> SEQ ID NO 11
<211> LENGTH: 65
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (36)..(36)
<223> OTHER INFORMATION: n denotes any nucleotide
<220> FEATURE:
<221> NAME/KEY: misc_feature
<222> LOCATION: (37)..(37)
<223> OTHER INFORMATION: n denotes any nucleotide

<400> SEQUENCE: 11
cagcttgctc gagtgtggca cttggcgaag ggctsnntcc taaactcaaa ttagcaacgt    60
gcatg                                                               65
```

<210> SEQ ID NO 12
<211> LENGTH: 41
<212> TYPE: DNA
<213> ORGANISM: Artificial Sequence
<220> FEATURE:
<223> OTHER INFORMATION: Primer

<400> SEQUENCE: 12
gttgctgtcc tcgatacagg gatatccact catccagatc t         41

<210> SEQ ID NO 13
<211> LENGTH: 65
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (33)..(33)
<223> OTHER INFORMATION: n denotes any nucleotide
<220> FEATURE:
<221> NAME/KEY: misc_feature
<222> LOCATION: (34)..(34)
<223> OTHER INFORMATION: n denotes any nucleotide

<400> SEQUENCE: 13
cagcttgctc gagtgtggca cttggcgaag gsnngcttcc taaactcaaa ttagcaacgt         60
gcatg         65

<210> SEQ ID NO 14
<211> LENGTH: 41
<212> TYPE: DNA
<213> ORGANISM: Artificial Sequence
<220> FEATURE:
<223> OTHER INFORMATION: Primer

<400> SEQUENCE: 14
gttgctgtcc tcgatacagg gatatccact catccagatc t         41

<210> SEQ ID NO 15
<211> LENGTH: 65
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (30)..(30)
<223> OTHER INFORMATION: n denotes any nucleotide
<220> FEATURE:
<221> NAME/KEY: misc_feature
<222> LOCATION: (31)..(31)
<223> OTHER INFORMATION: n denotes any nucleotide

<400> SEQUENCE: 15
cagcttgctc gagtgtggca cttggcgasn nagggcttcc taaactcaaa ttagcaacgt         60
gcatg         65

<210> SEQ ID NO 16
<211> LENGTH: 41
<212> TYPE: DNA
<213> ORGANISM: Artificial Sequence
<220> FEATURE:
<223> OTHER INFORMATION: Primer

<400> SEQUENCE: 16
gttgctgtcc tcgatacagg gatatccact catccagatc t         41

<210> SEQ ID NO 17
<211> LENGTH: 65
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (27)..(27)
<223> OTHER INFORMATION: n denotes any nucleotide
<220> FEATURE:
<221> NAME/KEY: misc_feature
<222> LOCATION: (28)..(28)
<223> OTHER INFORMATION: n denotes any nucleotide

<400> SEQUENCE: 17
cagcttgctc gagtgtggca cttggsnncg aagggcttcc taaactcaaa ttagcaacgt    60
gcatg    65

<210> SEQ ID NO 18
<211> LENGTH: 41
<212> TYPE: DNA
<213> ORGANISM: Artificial Sequence
<220> FEATURE:
<223> OTHER INFORMATION: Primer

<400> SEQUENCE: 18
gttgctgtcc tcgatacagg gatatccact catccagatc t    41

<210> SEQ ID NO 19
<211> LENGTH: 65
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (24)..(24)
<223> OTHER INFORMATION: n denotes any nucleotide
<220> FEATURE:
<221> NAME/KEY: misc_feature
<222> LOCATION: (25)..(25)
<223> OTHER INFORMATION: n denotes any nucleotide

<400> SEQUENCE: 19
cagcttgctc gagtgtggca ctsnntggcg aagggcttcc taaactcaaa ttagcaacgt    60
gcatg    65

<210> SEQ ID NO 20
<211> LENGTH: 41
<212> TYPE: DNA
<213> ORGANISM: Artificial Sequence
<220> FEATURE:
<223> OTHER INFORMATION: Primer

<400> SEQUENCE: 20
gttgctgtcc tcgatacagg gatatccact catccagatc t    41

<210> SEQ ID NO 21
<211> LENGTH: 65
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (21)..(21)
<223> OTHER INFORMATION: n denotes any nucleotide

```
<220> FEATURE:
<221> NAME/KEY: misc_feature
<222> LOCATION: (22)..(22)
<223> OTHER INFORMATION: n denotes any nucleotide

<400> SEQUENCE: 21
cagcttgctc gagtgtggcs nnacttggcg aagggcttcc taaactcaaa ttagcaacgt    60
gcatg                                                                65

<210> SEQ ID NO 22
<211> LENGTH: 41
<212> TYPE: DNA
<213> ORGANISM: Artificial Sequence
<220> FEATURE:
<223> OTHER INFORMATION: Primer

<400> SEQUENCE: 22
gttgctgtcc tcgatacagg gatatccact catccagatc t                        41

<210> SEQ ID NO 23
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (126)..(126)
<223> OTHER INFORMATION: Xaa denotes any amino acid

<400> SEQUENCE: 23
```

Ala Gln Thr Val Pro Tyr Gly Ile Pro Leu Ile Lys Ala Asp Lys Val
 1               5                  10                  15

Gln Ala Gln Gly Phe Lys Gly Ala Asn Val Lys Val Ala Val Leu Asp
                20                  25                  30

Thr Gly Ile Gln Ala Ser His Pro Asp Leu Asn Val Val Gly Gly Ala
            35                  40                  45

Ser Phe Val Ala Gly Glu Ala Tyr Asn Thr Asp Gly Asn Gly His Gly
        50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Thr Tyr Ser Gly Ile Val Ser Gly Ile Glu Trp
            100                 105                 110

Ala Thr Thr Asn Gly Met Asp Ala Val Ile Asn Met Ser Xaa Leu Gly
        115                 120                 125

Gly Pro Ser Gly Ser Thr Ala Met Lys Gln Ala Val Asp Asn Ala Tyr
    130                 135                 140

Ala Arg Gly Val Val Val Ala Ala Gly Asn Ser Gly Ser Ser
145                 150                 155                 160

Gly Asn Thr Asn Thr Ile Gly Tyr Pro Ala Lys Tyr Asp Ser Val Ile
                165                 170                 175

Ala Val Gly Ala Val Asp Ser Asn Ser Asn Arg Ala Ser Phe Ser Ser
            180                 185                 190

Val Gly Ala Glu Leu Glu Val Met Ala Pro Gly Ala Gly Val Tyr Ser
        195                 200                 205

Thr Tyr Pro Thr Ser Thr Tyr Ala Thr Leu Asn Gly Thr Ser Met Ala
    210                 215                 220

```
Ser Pro His Val Ala Gly Ala Ala Leu Ile Leu Ser Lys His Pro
225                 230                 235                 240

Asn Leu Ser Ala Ser Gln Val Arg Asn Arg Leu Ser Ser Thr Ala Thr
                245                 250                 255

Tyr Leu Gly Ser Ser Phe Tyr Tyr Gly Lys Gly Leu Ile Asn Val Glu
            260                 265                 270

Ala Ala Ala Gln
        275
```

<210> SEQ ID NO 24
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (125)..(125)
<223> OTHER INFORMATION: Xaa denotes any amino acid

<400> SEQUENCE: 24

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Ala Val Ala Asn Leu Ser Xaa Leu Gly Ser
        115                 120                 125

Pro Ser Pro Ser Ala Thr Leu Glu Gln Ala Val Asn Ser Ala Thr Ser
    130                 135                 140

Arg Gly Val Leu Val Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
        195                 200                 205

Thr Tyr Ala Ser Leu Asn Gly Thr Ser Met Ala Thr Pro His Val Ala
    210                 215                 220

Gly Ala Ala Ala Leu Val Lys Gln Lys Asn Pro Ser Trp Ser Asn Val
225                 230                 235                 240

Gln Ile Arg Asn His Leu Lys Asn Thr Ala Thr Ser Leu Gly Ser Thr
                245                 250                 255

Asn Leu Tyr Gly Ser Gly Leu Val Asn Ala Glu Ala Ala Thr Arg
            260                 265                 270
```

<210> SEQ ID NO 25

<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (127)..(127)
<223> OTHER INFORMATION: Xaa denotes any amino acid

<400> SEQUENCE: 25

```
Ala Gln Thr Val Pro Tyr Gly Ile Pro Leu Ile Lys Ala Asp Lys Val
1               5                  10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
 50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Thr Tyr Ser Gly Ile Val Ser Gly Ile Glu Trp
            100                 105                 110

Ala Thr Thr Asn Gly Met Asp Ala Val Ile Asn Met Ser Leu Xaa Gly
        115                 120                 125

Gly Pro Ser Gly Ser Thr Ala Met Lys Gln Ala Val Asp Asn Ala Tyr
    130                 135                 140

Ala Arg Gly Val Val Val Ala Ala Gly Asn Ser Gly Ser Ser
145                 150                 155                 160

Gly Asn Thr Asn Thr Ile Gly Tyr Pro Ala Lys Tyr Asp Ser Val Ile
                165                 170                 175

Ala Val Gly Ala Val Asp Ser Asn Ser Asn Arg Ala Ser Phe Ser Ser
            180                 185                 190

Val Gly Ala Glu Leu Glu Val Met Ala Pro Gly Ala Gly Val Tyr Ser
        195                 200                 205

Thr Tyr Pro Thr Ser Thr Tyr Ala Thr Leu Asn Gly Thr Ser Met Ala
    210                 215                 220

Ser Pro His Val Ala Gly Ala Ala Leu Ile Leu Ser Lys His Pro
225                 230                 235                 240

Asn Leu Ser Ala Ser Gln Val Arg Asn Arg Leu Ser Ser Thr Ala Thr
                245                 250                 255

Tyr Leu Gly Ser Ser Phe Tyr Tyr Gly Lys Gly Leu Ile Asn Val Glu
            260                 265                 270

Ala Ala Ala Gln
        275
```

<210> SEQ ID NO 26
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (126)..(126)
<223> OTHER INFORMATION: Xaa denotes any amino acid

<400> SEQUENCE: 26

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
                100                 105                 110

Gly Asn Asn Gly Met His Ala Val Ala Asn Leu Ser Leu Xaa Gly Ser
            115                 120                 125

Pro Ser Pro Ser Ala Thr Leu Glu Gln Ala Val Asn Ser Ala Thr Ser
130                 135                 140

Arg Gly Val Leu Val Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
            195                 200                 205

Thr Tyr Ala Ser Leu Asn Gly Thr Ser Met Ala Thr Pro His Val Ala
            210                 215                 220

Gly Ala Ala Ala Leu Val Lys Gln Lys Asn Pro Ser Trp Ser Asn Val
225                 230                 235                 240

Gln Ile Arg Asn His Leu Lys Asn Thr Ala Thr Ser Leu Gly Ser Thr
            245                 250                 255

Asn Leu Tyr Gly Ser Gly Leu Val Asn Ala Glu Ala Ala Thr Arg
            260                 265                 270

<210> SEQ ID NO 27
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (128)..(128)
<223> OTHER INFORMATION: Xaa denotes any amino acid

<400> SEQUENCE: 27

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
            35                  40                  45

Ser Phe Val Ala Gly Glu Ala Tyr Asn Thr Asp Gly Asn Gly His Gly
50                  55                  60

Thr His Val Ala Gly Thr Val Ala Ala Leu Asp Asn Thr Thr Gly Val

```
            65                  70                  75                  80
Leu Gly Val Ala Pro Ser Val Ser Leu Tyr Ala Val Lys Val Leu Asn
                85                  90                  95

Ser Ser Gly Ser Gly Thr Tyr Ser Gly Ile Val Ser Gly Ile Glu Trp
            100                 105                 110

Ala Thr Thr Asn Gly Met Asp Ala Val Ile Asn Met Ser Leu Gly Xaa
            115                 120                 125

Gly Pro Ser Gly Ser Thr Ala Met Lys Gln Ala Val Asp Asn Ala Tyr
            130                 135                 140

Ala Arg Gly Val Val Val Ala Ala Gly Asn Ser Gly Ser Ser
145                 150                 155                 160

Gly Asn Thr Asn Thr Ile Gly Tyr Pro Ala Lys Tyr Asp Ser Val Ile
                165                 170                 175

Ala Val Gly Ala Val Asp Ser Asn Ser Asn Arg Ala Ser Phe Ser Ser
                180                 185                 190

Val Gly Ala Glu Leu Glu Val Met Ala Pro Gly Ala Gly Val Tyr Ser
                195                 200                 205

Thr Tyr Pro Thr Ser Thr Tyr Ala Thr Leu Asn Gly Thr Ser Met Ala
            210                 215                 220

Ser Pro His Val Ala Gly Ala Ala Leu Ile Leu Ser Lys His Pro
225                 230                 235                 240

Asn Leu Ser Ala Ser Gln Val Arg Asn Arg Leu Ser Ser Thr Ala Thr
                245                 250                 255

Tyr Leu Gly Ser Ser Phe Tyr Tyr Gly Lys Gly Leu Ile Asn Val Glu
            260                 265                 270

Ala Ala Ala Gln
        275

<210> SEQ ID NO 28
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (127)..(127)
<223> OTHER INFORMATION: Xaa denotes any amino acid

<400> SEQUENCE: 28

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Ala Val Ala Asn Leu Ser Leu Gly Xaa Ser
            115                 120                 125
```

```
Pro Ser Pro Ser Ala Thr Leu Glu Gln Ala Val Asn Ser Ala Thr Ser
    130                 135                 140

Arg Gly Val Leu Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
            195                 200                 205

Thr Tyr Ala Ser Leu Asn Gly Thr Ser Met Ala Thr Pro His Val Ala
    210                 215                 220

Gly Ala Ala Leu Val Lys Gln Lys Asn Pro Ser Trp Ser Asn Val
225                 230                 235                 240

Gln Ile Arg Asn His Leu Lys Asn Thr Ala Thr Ser Leu Gly Ser Thr
                245                 250                 255

Asn Leu Tyr Gly Ser Gly Leu Val Asn Ala Glu Ala Ala Thr Arg
            260                 265                 270

<210> SEQ ID NO 29
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (129)..(129)
<223> OTHER INFORMATION: Xaa denotes any amino acid

<400> SEQUENCE: 29

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Thr Tyr Ser Gly Ile Val Ser Gly Ile Glu Trp
            100                 105                 110

Ala Thr Thr Asn Gly Met Asp Ala Val Ile Asn Met Ser Leu Gly Gly
        115                 120                 125

Xaa Pro Ser Gly Ser Thr Ala Met Lys Gln Ala Val Asp Asn Ala Tyr
    130                 135                 140

Ala Arg Gly Val Val Val Ala Ala Gly Asn Ser Gly Ser Ser
145                 150                 155                 160

Gly Asn Thr Asn Thr Ile Gly Tyr Pro Ala Lys Tyr Asp Ser Val Ile
                165                 170                 175

Ala Val Gly Ala Val Asp Ser Asn Ser Asn Arg Ala Ser Phe Ser Ser
            180                 185                 190

Val Gly Ala Glu Leu Glu Val Met Ala Pro Gly Ala Gly Val Tyr Ser
        195                 200                 205
```

Thr Tyr Pro Thr Ser Thr Tyr Ala Thr Leu Asn Gly Thr Ser Met Ala
              210                 215                 220

Ser Pro His Val Ala Gly Ala Ala Leu Ile Leu Ser Lys His Pro
225                 230                 235                 240

Asn Leu Ser Ala Ser Gln Val Arg Asn Arg Leu Ser Ser Thr Ala Thr
                245                 250                 255

Tyr Leu Gly Ser Ser Phe Tyr Tyr Gly Lys Gly Leu Ile Asn Val Glu
                260                 265                 270

Ala Ala Ala Gln
            275

<210> SEQ ID NO 30
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (128)..(128)
<223> OTHER INFORMATION: Xaa denotes any amino acid

<400> SEQUENCE: 30

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
                100                 105                 110

Gly Asn Asn Gly Met His Ala Val Ala Asn Leu Ser Leu Gly Ser Xaa
            115                 120                 125

Pro Ser Pro Ser Ala Thr Leu Glu Gln Ala Val Asn Ser Ala Thr Ser
        130                 135                 140

Arg Gly Val Leu Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
        195                 200                 205

Thr Tyr Ala Ser Leu Asn Gly Thr Ser Met Ala Thr Pro His Val Ala
    210                 215                 220

Gly Ala Ala Ala Leu Val Lys Gln Lys Asn Pro Ser Trp Ser Asn Val
225                 230                 235                 240

Gln Ile Arg Asn His Leu Lys Asn Thr Ala Thr Ser Leu Gly Ser Thr
                245                 250                 255

Asn Leu Tyr Gly Ser Gly Leu Val Asn Ala Glu Ala Ala Thr Arg

-continued

```
                    260                 265                 270

<210> SEQ ID NO 31
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (130)..(130)
<223> OTHER INFORMATION: Xaa denotes any amino acid

<400> SEQUENCE: 31

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Thr Tyr Ser Gly Ile Val Ser Gly Ile Glu Trp
            100                 105                 110

Ala Thr Thr Asn Gly Met Asp Ala Val Ile Asn Met Ser Leu Gly Gly
        115                 120                 125

Pro Xaa Ser Gly Ser Thr Ala Met Lys Gln Ala Val Asp Asn Ala Tyr
    130                 135                 140

Ala Arg Gly Val Val Val Ala Ala Ala Gly Asn Ser Gly Ser Ser
145                 150                 155                 160

Gly Asn Thr Asn Thr Ile Gly Tyr Pro Ala Lys Tyr Asp Ser Val Ile
                165                 170                 175

Ala Val Gly Ala Val Asp Ser Asn Ser Asn Arg Ala Ser Phe Ser Ser
            180                 185                 190

Val Gly Ala Glu Leu Glu Val Met Ala Pro Gly Ala Gly Val Tyr Ser
        195                 200                 205

Thr Tyr Pro Thr Ser Thr Tyr Ala Thr Leu Asn Gly Thr Ser Met Ala
    210                 215                 220

Ser Pro His Val Ala Gly Ala Ala Leu Ile Leu Ser Lys His Pro
225                 230                 235                 240

Asn Leu Ser Ala Ser Gln Val Arg Asn Arg Leu Ser Ser Thr Ala Thr
                245                 250                 255

Tyr Leu Gly Ser Ser Phe Tyr Tyr Gly Lys Gly Leu Ile Asn Val Glu
            260                 265                 270

Ala Ala Ala Gln
        275

<210> SEQ ID NO 32
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

<222> LOCATION: (129)..(129)
<223> OTHER INFORMATION: Xaa denotes any amino acid

<400> SEQUENCE: 32

```
Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Ala Val Ala Asn Leu Ser Leu Gly Ser Pro
        115                 120                 125

Xaa Ser Pro Ser Ala Thr Leu Glu Gln Ala Val Asn Ser Ala Thr Ser
130                 135                 140

Arg Gly Val Leu Val Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
        195                 200                 205

Thr Tyr Ala Ser Leu Asn Gly Thr Ser Met Ala Thr Pro His Val Ala
210                 215                 220

Gly Ala Ala Ala Leu Val Lys Gln Lys Asn Pro Ser Trp Ser Asn Val
225                 230                 235                 240

Gln Ile Arg Asn His Leu Lys Asn Thr Ala Thr Ser Leu Gly Ser Thr
                245                 250                 255

Asn Leu Tyr Gly Ser Gly Leu Val Asn Ala Glu Ala Ala Thr Arg
            260                 265                 270
```

<210> SEQ ID NO 33
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (131)..(131)
<223> OTHER INFORMATION: Xaa denotes any amino acid

<400> SEQUENCE: 33

```
Ala Gln Thr Val Pro Tyr Gly Ile Pro Leu Ile Lys Ala Asp Lys Val
 1               5                  10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45
```

```
Ser Phe Val Ala Gly Glu Ala Tyr Asn Thr Asp Gly Asn Gly His Gly
 50                  55                  60

Thr His Val Ala Gly Thr Val Ala Ala Leu Asp Asn Thr Thr Gly Val
 65                  70                  75                  80

Leu Gly Val Ala Pro Ser Val Ser Leu Tyr Ala Val Lys Val Leu Asn
                 85                  90                  95

Ser Ser Gly Ser Gly Thr Tyr Ser Gly Ile Val Ser Gly Ile Glu Trp
                100                 105                 110

Ala Thr Thr Asn Gly Met Asp Ala Val Ile Asn Met Ser Leu Gly Gly
                115                 120                 125

Pro Ser Xaa Gly Ser Thr Ala Met Lys Gln Ala Val Asp Asn Ala Tyr
        130                 135                 140

Ala Arg Gly Val Val Val Ala Ala Gly Asn Ser Gly Ser Ser
145                 150                 155                 160

Gly Asn Thr Asn Thr Ile Gly Tyr Pro Ala Lys Tyr Asp Ser Val Ile
                165                 170                 175

Ala Val Gly Ala Val Asp Ser Asn Ser Asn Arg Ala Ser Phe Ser Ser
                180                 185                 190

Val Gly Ala Glu Leu Glu Val Met Ala Pro Gly Ala Gly Val Tyr Ser
                195                 200                 205

Thr Tyr Pro Thr Ser Thr Tyr Ala Thr Leu Asn Gly Thr Ser Met Ala
210                 215                 220

Ser Pro His Val Ala Gly Ala Ala Leu Ile Leu Ser Lys His Pro
225                 230                 235                 240

Asn Leu Ser Ala Ser Gln Val Arg Asn Arg Leu Ser Ser Thr Ala Thr
                245                 250                 255

Tyr Leu Gly Ser Ser Phe Tyr Tyr Gly Lys Gly Leu Ile Asn Val Glu
                260                 265                 270

Ala Ala Ala Gln
        275

<210> SEQ ID NO 34
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (130)..(130)
<223> OTHER INFORMATION: Xaa denotes any amino acid

<400> SEQUENCE: 34

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
                 20                  25                  30

Thr Gly Ile Ser Thr His Pro Asp Leu Asn Ile Arg Gly Gly Ala Ser
             35                  40                  45

Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Ser Gly Ser Gly Ser Val Ser Ser Ile Ala Gln Gly Leu Glu Trp Ala
                100                 105                 110
```

```
Gly Asn Asn Gly Met His Ala Val Ala Asn Leu Ser Leu Gly Ser Pro
            115                 120                 125

Ser Xaa Pro Ser Ala Thr Leu Glu Gln Ala Val Asn Ser Ala Thr Ser
    130                 135                 140

Arg Gly Val Leu Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
            195                 200                 205

Thr Tyr Ala Ser Leu Asn Gly Thr Ser Met Ala Thr Pro His Val Ala
            210                 215                 220

Gly Ala Ala Leu Val Lys Gln Lys Asn Pro Ser Trp Ser Asn Val
225                 230                 235                 240

Gln Ile Arg Asn His Leu Lys Asn Thr Ala Thr Ser Leu Gly Ser Thr
            245                 250                 255

Asn Leu Tyr Gly Ser Gly Leu Val Asn Ala Glu Ala Ala Thr Arg
            260                 265                 270
```

<210> SEQ ID NO 35
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (132)..(132)
<223> OTHER INFORMATION: Xaa denotes any amino acid

<400> SEQUENCE: 35

```
Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
            35                  40                  45

Ser Phe Val Ala Gly Glu Ala Tyr Asn Thr Asp Gly Asn His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Thr Tyr Ser Gly Ile Val Ser Gly Ile Glu Trp
            100                 105                 110

Ala Thr Thr Asn Gly Met Asp Ala Val Ile Asn Met Ser Leu Gly Gly
            115                 120                 125

Pro Ser Gly Xaa Ser Thr Ala Met Lys Gln Ala Val Asp Asn Ala Tyr
            130                 135                 140

Ala Arg Gly Val Val Val Ala Ala Gly Asn Ser Gly Ser Ser
145                 150                 155                 160

Gly Asn Thr Asn Thr Ile Gly Tyr Pro Ala Lys Tyr Asp Ser Val Ile
            165                 170                 175

Ala Val Gly Ala Val Asp Ser Asn Ser Asn Arg Ala Ser Phe Ser Ser
```

```
                        180                 185                 190
Val Gly Ala Glu Leu Glu Val Met Ala Pro Gly Ala Gly Val Tyr Ser
            195                 200                 205

Thr Tyr Pro Thr Ser Thr Tyr Ala Thr Leu Asn Gly Thr Ser Met Ala
        210                 215                 220

Ser Pro His Val Ala Gly Ala Ala Leu Ile Leu Ser Lys His Pro
225                 230                 235                 240

Asn Leu Ser Ala Ser Gln Val Arg Asn Arg Leu Ser Ser Thr Ala Thr
                245                 250                 255

Tyr Leu Gly Ser Ser Phe Tyr Tyr Gly Lys Gly Leu Ile Asn Val Glu
            260                 265                 270

Ala Ala Ala Gln
        275

<210> SEQ ID NO 36
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (131)..(131)
<223> OTHER INFORMATION: Xaa denotes any amino acid

<400> SEQUENCE: 36

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Ala Val Ala Asn Leu Ser Leu Gly Ser Pro
        115                 120                 125

Ser Pro Xaa Ser Ala Thr Leu Glu Gln Ala Val Asn Ser Ala Thr Ser
    130                 135                 140

Arg Gly Val Leu Val Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
        195                 200                 205

Thr Tyr Ala Ser Leu Asn Gly Thr Ser Met Ala Thr Pro His Val Ala
    210                 215                 220

Gly Ala Ala Ala Leu Val Lys Gln Lys Asn Pro Ser Trp Ser Asn Val
225                 230                 235                 240
```

```
Gln Ile Arg Asn His Leu Lys Asn Thr Ala Thr Ser Leu Gly Ser Thr
                245                 250                 255

Asn Leu Tyr Gly Ser Gly Leu Val Asn Ala Glu Ala Ala Thr Arg
            260                 265                 270
```

<210> SEQ ID NO 37
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (133)..(133)
<223> OTHER INFORMATION: Xaa denotes any amino acid

<400> SEQUENCE: 37

```
Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
                20                  25                  30

Thr Gly Ile Gln Ala Ser His Pro Asp Leu Asn Val Val Gly Gly Ala
            35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Thr Tyr Ser Gly Ile Val Ser Gly Ile Glu Trp
                100                 105                 110

Ala Thr Thr Asn Gly Met Asp Ala Val Ile Asn Met Ser Leu Gly Gly
            115                 120                 125

Pro Ser Gly Ser Xaa Thr Ala Met Lys Gln Ala Val Asp Asn Ala Tyr
    130                 135                 140

Ala Arg Gly Val Val Val Ala Ala Ala Gly Asn Ser Gly Ser Ser
145                 150                 155                 160

Gly Asn Thr Asn Thr Ile Gly Tyr Pro Ala Lys Tyr Asp Ser Val Ile
                165                 170                 175

Ala Val Gly Ala Val Asp Ser Asn Ser Asn Arg Ala Ser Phe Ser Ser
            180                 185                 190

Val Gly Ala Glu Leu Glu Val Met Ala Pro Gly Ala Gly Val Tyr Ser
        195                 200                 205

Thr Tyr Pro Thr Ser Thr Tyr Ala Thr Leu Asn Gly Thr Ser Met Ala
    210                 215                 220

Ser Pro His Val Ala Gly Ala Ala Leu Ile Leu Ser Lys His Pro
225                 230                 235                 240

Asn Leu Ser Ala Ser Gln Val Arg Asn Arg Leu Ser Ser Thr Ala Thr
                245                 250                 255

Tyr Leu Gly Ser Ser Phe Tyr Tyr Gly Lys Gly Leu Ile Asn Val Glu
            260                 265                 270

Ala Ala Ala Gln
        275
```

<210> SEQ ID NO 38
<211> LENGTH: 271
<212> TYPE: PRT
<213> ORGANISM: Artificial Sequence

```
-continued

<220> FEATURE:
<223> OTHER INFORMATION: Synthetic
<220> FEATURE:
<221> NAME/KEY: misc_feature
<222> LOCATION: (132)..(132)
<223> OTHER INFORMATION: Xaa denotes any amino acid

<400> SEQUENCE: 38

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
     50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Ala Val Ala Asn Leu Ser Leu Gly Ser Pro
            115                 120                 125

Ser Pro Ser Xaa Ala Thr Leu Glu Gln Ala Val Asn Ser Ala Thr Ser
    130                 135                 140

Arg Gly Val Leu Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
        195                 200                 205

Thr Tyr Ala Ser Leu Asn Gly Thr Ser Met Ala Thr Pro His Val Ala
    210                 215                 220

Gly Ala Ala Ala Leu Val Lys Gln Lys Asn Pro Ser Trp Ser Asn Val
225                 230                 235                 240

Gln Ile Arg Asn His Leu Lys Asn Thr Ala Thr Ser Leu Gly Ser Thr
                245                 250                 255

Asn Leu Tyr Gly Ser Gly Leu Val Asn Ala Glu Ala Ala Thr Arg
            260                 265                 270
```